United States Patent
Cheung et al.

(10) Patent No.: US 10,106,773 B2
(45) Date of Patent: Oct. 23, 2018

(54) ISOLATION AND USE OF PLURIPOTENT STEM CELL POPULATION FROM ADULT NEURAL CREST-DERIVED TISSUES

(71) Applicant: UNIVERSITY OF MIAMI, Miami, FL (US)

(72) Inventors: Herman S. Cheung, Miami, FL (US); Daniel Pelaez, Miami, FL (US); C-Y Charles Huang, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 408 days.

(21) Appl. No.: 14/382,287

(22) PCT Filed: Mar. 1, 2013

(86) PCT No.: PCT/US2013/028686
§ 371 (c)(1),
(2) Date: Aug. 29, 2014

(87) PCT Pub. No.: WO2013/131012
PCT Pub. Date: Sep. 6, 2013

(65) Prior Publication Data
US 2015/0044180 A1    Feb. 12, 2015

Related U.S. Application Data

(60) Provisional application No. 61/605,483, filed on Mar. 1, 2012.

(51) Int. Cl.
| | |
|---|---|
| *C12N 5/0797* | (2010.01) |
| *G01N 33/68* | (2006.01) |
| *C07K 14/705* | (2006.01) |
| *C12N 5/074* | (2010.01) |
| *C12N 5/079* | (2010.01) |
| *C12N 5/0793* | (2010.01) |
| *A61K 35/545* | (2015.01) |
| *A61K 35/30* | (2015.01) |

(52) U.S. Cl.
CPC ............ *C12N 5/0623* (2013.01); *A61K 35/30* (2013.01); *A61K 35/545* (2013.01); *C12N 5/062* (2013.01); *C12N 5/0607* (2013.01); *C12N 5/0618* (2013.01); *G01N 33/68* (2013.01); *C12N 2501/105* (2013.01); *C12N 2501/11* (2013.01); *C12N 2501/115* (2013.01); *C12N 2501/155* (2013.01); *C12N 2501/415* (2013.01); *C12N 2506/03* (2013.01)

(58) Field of Classification Search
CPC .. C07K 14/70596; C07K 16/28; A61K 35/30; A61K 35/545; C12N 2506/03; C12N 5/0618; C12N 5/0623; G01N 33/68
USPC ................ 435/368, 378, 7.1, 7.21; 424/93.7
See application file for complete search history.

(56) References Cited

U.S. PATENT DOCUMENTS

| | | | |
|---|---|---|---|
| 7,541,186 B2 | 6/2009 | Reh et al. | |
| 2009/0258421 A1 | 10/2009 | Reubinoff et al. | |
| 2009/0269845 A1* | 10/2009 | Rezania ............... | C12N 5/0606 435/366 |
| 2011/0236356 A1* | 9/2011 | Huang ................ | C12N 5/0607 424/93.7 |

FOREIGN PATENT DOCUMENTS

| | | |
|---|---|---|
| WO | WO 2009/136283 A2 | 11/2009 |
| WO | WO 2013/131012 A1 | 9/2013 |

OTHER PUBLICATIONS

Chen et al. (2006) Stem Cells, vol. 24(5), 1265-1273.*
Achilleos et al. (2012) Cell Research, vol. 22, 288-304.*
Chew et al., "Role of connexin43 in central nervous system injury," Exp. Neurol. 255(2):250-261 (2010).
International Search Report, PCT appl. No. PCT/US2013/028686, 4 pages (dated Jun. 4, 2013).
Written Opinion of the International Searching Authority, PCT appl. No. PCT/US2013/028686, 7 pages (dated Jun. 4, 2013).
International Preliminary Report on Patentability, PCT appl. No. PCT/US2013/028686, dated Sep. 2, 2014, 8 pages.

\* cited by examiner

*Primary Examiner* — Anne Marie S Wehbe
(74) *Attorney, Agent, or Firm* — Ballard Spahr LLP

(57) ABSTRACT

The present invention relates to methods of isolating a substantially homogeneous population of pluripotent stem cells from adult neural crest tissue (e.g., periodontal ligament) as well as pharmaceutical compositions comprising such isolated pluripotent stem cells. Methods of inducing the isolated pluripotent stem cells into specific cell lineages, such as neurogenic and retinogenic lineages, are also described. The isolated pluripotent stem cells find use in various regenerative medicine applications and the treatment of degenerative diseases.

7 Claims, 21 Drawing Sheets
Specification includes a Sequence Listing.

ISOLATION AND USE OF PLURIPOTENT STEM CELL POPULATION FROM ADULT NEURAL CREST-DERIVED TISSUES

CROSS-REFERENCE TO RELATED APPLICATIONS

This application claims priority to U.S. Provisional Application No. 61/605,483, filed Mar. 1, 2012, which is hereby incorporated by reference in its entirety.

STATEMENT OF GOVERNMENT SUPPORT

This invention was made in part with government support from the Veterans Affairs Department. The U.S. government has certain rights in the invention.

REFERENCE TO A SEQUENCE LISTING

The Sequence Listing submitted herewith as a text file named "37559_0040U2_SL.txt," created on Aug. 2, 2018, and having a size of 12,288 bytes is hereby incorporated by reference pursuant to 37 C.F.R. § 1.52(e)(5).

FIELD OF THE INVENTION

The present invention relates generally to the fields of stem cell biology and regenerative medicine, and more particularly to the isolation and uses of a specific population of pluripotent, neural crest-derived stem cells. The invention also relates to methods of pre-conditioning these pluripotent stem cells to differentiate into specific cell lineages for different regenerative medicine applications, such as the treatment of degenerative diseases.

BACKGROUND OF THE INVENTION

Cellular potency, or the potential for a cell to differentiate down various tissue lineages, is the defining characteristic as to the viability of the cell source for a given application. With the establishment of embryonic stem cell lines, the idea of utilizing pluripotent cell sources for regenerative medical applications was introduced as a promising alternative to traditional medical practices. However, there are ethical dilemmas as well as immunological concerns arising from the use of embryonic cell sources in clinical settings. The advent of induced pluripotent stem cells (iPSCs) attempted to circumvent both of these issues and brought the concept of patient-specific pluripotent stem cell attainment to the forefront of the field (Takahashi et al., 2007). This iPSC technology, however, is not without its drawbacks; still in its early stages, the scientific community is trying to decipher the mechanisms underlying the induction of pluripotency (Rezanejad et al., 2012) and overcome the aberrant epigenetic changes arising from the implementation of the technique (Ruiz et al., 2012). Nevertheless, the potential of obtaining pluripotent stem cells from adult tissues is of significant importance and remains as the ultimate goal in overcoming the limitations presently found with other postnatal stem cell populations.

Researchers have worked on the identification and isolation of remnant embryonic-like cells from adult tissues (Conrad et al., 2008; Wagers et al., 2004; Jiang et al., 2002). One of the main focuses has been on tissues arising from the neural crest (Coura et al., 2008; Dupin et al., 2012). Neural crest cells are a population of multipotent and migratory cells that originate from the neural folds during vertebrate development. They are capable of differentiating into diverse cell lineages with regards to the positioning along the anterior-posterior axis (Taneyhill et al., 2008). Beside the specification to cranial ganglia, craniofacial cartilages and bones, thymus, middle ear bones and jaws, the cranial neural crest cells migrating to the pharyngeal pouches and arches can contribute to tooth formation (Degistirici et al., 2008). They give rise to most dental tissues including odontoblasts, dental pulp, apical papilla, dental follicle and periodontal ligament (PDL). PDL is a soft connective tissue located between the root of tooth and alveolar bone socket. It contains a mixed population of fibroblasts, epithelial, undifferentiated mesenchymal, bone and cememtum cells, sitting in the hydrated extracellular ground substance with collagen-rich fibrils. Apart from fixing the tooth to the alveolar bone and withstanding the compressive force during the chewing motion, PDL provides sensory, nutritive and homeostatic support to the alveolar compartment.

Seo and colleagues found that enzymatic treatment of human PDL released a postnatal stem cell population capable of clonogenic growth (Seo et al., 2004). These undifferentiated cells express markers of mesenchymal stem cells (STRO-1, scleraxis), embryonic stem cells (Oct4, Sox2, Nanog and Klf4) and neural crest cells (nestin, Slug, p75 neurotrophin receptor, Sox10), reflecting their pluripotent characteristics, and can differentiate to neurogenic, cardiomyogenic, chondrogenic and osteogenic lineages (Huang et al., 2009; Song et al., 2012; Coura et al., 2008). Given their easy accessibility and vast differentiation potential, PDL-derived stem cells could be an important cell source for regenerative medicine. However, there remains a need in the art for methods of isolating a homogeneous population of pluripotent stem cells from neural crest tissue, like the periodontal ligament, as well as methods of conditioning these pluripotent stem cells to differentiate into desired cell lineages for specific regenerative medicine applications.

SUMMARY OF THE INVENTION

The present invention is based, in part, on the discovery that connexin 43 can be used as a selection marker to obtain a substantially homogeneous population of pluripotent stem cells from neural crest tissue, such as the adult periodontal ligament. Accordingly, the present invention provides a method of selecting and isolating pluripotent stem cells from neural crest-derived tissue and using such isolated stem cells in the repair of damaged tissues and the treatment of various degenerative diseases.

In one embodiment, the method of isolating pluripotent stem cells comprises extracting cells from tissue derived from the neural crest, culturing said extracted cells under adherent conditions, and isolating said cultured cells that express Connexin-43, wherein said isolated cells are pluripotent stem cells. Such isolated pluripotent stem cells are capable of differentiating into cells of the ectoderm, endoderm, and mesoderm lineages. In certain embodiments, the tissue derived from the neural crest is adult periodontal ligament. Expression of one or more stem cell markers (e.g., Oct4, Nanog, Sox2, Klf4) or neural crest markers (e.g., p75 neurotrophin receptor, Nestin, Sox10, N-Cadherin, Slug) may be assessed in the extracted or cultured cells prior to isolation.

The present invention also includes homogeneous and substantially pure populations of adult human pluripotent stem cells isolated by the selection methods of the invention. In some embodiments, the homogeneous or substantially pure population comprises pluripotent stem cells that are positive for at least one stem cell marker, express Connexin-43, are capable of differentiating into cells of the ectoderm, endoderm, and mesoderm lineages, and are isolated from human tissue derived from the neural crest. In certain embodiments, the pluripotent stem cells are isolated from adult human periodontal ligament. In other embodiments, 70% or greater of the pluripotent stem cells in the population are positive for Oct4. Pharmaceutical compositions comprising the homogeneous or substantially pure populations of adult pluripotent stem cells as wells as methods of making the pharmaceutical compositions are also encompassed by the present invention.

In another embodiment, the present invention provides methods of differentiating the pluripotent stem cells into specific cell lineages. In one embodiment, a method of differentiating pluripotent stem cells isolated from adult periodontal ligament to neural progenitor cells or neural cells is provided. In certain embodiments, the method comprises incubating the pluripotent stem cells in a culture media comprising epidermal growth factor (EGF) and basic fibroblast growth factor (bFGF) for a period of time, wherein a plurality of said pluripotent stem cells are differentiated into neural progenitor cells or neural cells at the end of the period of time.

In another embodiment, a method of differentiating pluripotent stem cells isolated from adult periodontal ligament to retinal progenitor cells or retinal cells is provided. The method comprises treating cells with Noggin, Dkk-1, and optionally insulin-like growth factor-1 (IGF-1). For instance, in certain embodiments, the method comprises culturing said pluripotent stem cells under non-adherent conditions in a first induction media comprising a first concentration of Noggin, a first concentration of Dkk-1, and IGF-1 for a first period of time to obtain neurospheres, and plating the spheres on a substrate in a second induction media comprising a second concentration of Noggin and a second concentration of Dkk-1 for a second period of time, wherein a plurality of said pluripotent stem cells are differentiated into retinal progenitor cells or retinal cells at the end of the second period of time. In some embodiments, the second concentrations of Noggin and Dkk-1 are higher (e.g. ten-fold) than the first concentrations of Noggin and Dkk-1.

Methods of repairing damaged tissue in a subject in need thereof by administering the isolated pluripotent stem cells or pharmaceutical compositions described herein are also provided by the present invention. The isolated pluripotent stem cells may optionally be preconditioned or induced to differentiate into specific cell lineages, such as neurogenic or retinogenic lineages, prior to administration to the subject. Damaged tissue that can be repaired by the methods of the invention include tissue damaged due to injury, ischemic events, or degenerative diseases or disorders. In certain embodiments, the pluripotent stem cells are isolated from the subject to whom they will be administered (i.e. the pluripotent stem cells are autologous).

DETAILED DESCRIPTION OF THE INVENTION

Figure 1:
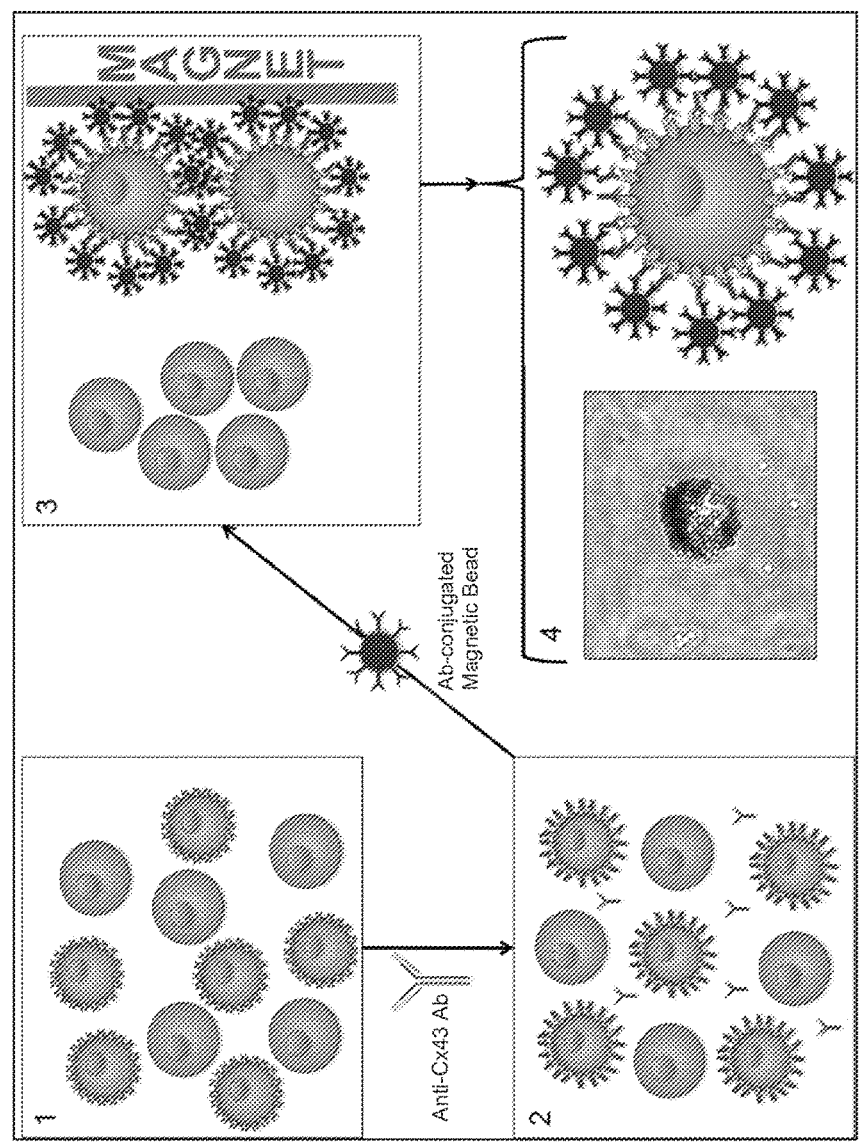
FIG. 1. Schematic of magnetic bead sorting technique. (1) Suspension of heterogeneous periodontal ligament-derived stem cell populations. (2) Labeling of Cx43 gap junction protein with primary antibody. (3) Appropriate anti-primary antibody conjugated magnetic iron bead incubation and magnetic separation of positively selected cells. (4) Selection of Cx43-positive cells and culture. Image: Brightfield image of cell surrounded by magnetic beads following selection.

The present invention is based, in part, on the discovery that connexin 43 can be used as a surface marker to select and isolate remnant neural crest pluripotent stem cells from adult human tissues, such as adult periodontal ligaments. The inventors have surprisingly found that selection of connexin 43-positive cells from adherent cultures of cells isolated from adult human periodontal ligaments results in a substantially homogeneous population of pluripotent, embryonic-like stem cells that are capable of generating cells from all three germ layers. The isolation methods of the invention allow for the creation of patient-specific cell lines from tissues that can be easily obtained from routine medical procedures. Such isolated pluripotent stem cells find use in various regenerative medicine applications, such as treatment of degenerative diseases and disorders.

In one embodiment, the present invention provides a method of isolating pluripotent stem cells comprising extracting cells from tissue derived from the neural crest, culturing said extracted cells under adherent conditions, and isolating said cultured cells that express Connexin-43, wherein said isolated cells are pluripotent stem cells. "Pluripotent stem cells" are stem cells that have the potential to differentiate into any of the three germ layers: endoderm (e.g., interior stomach lining, gastrointestinal tract, the lungs), mesoderm (e.g., muscle, bone, blood, urogenital), or ectoderm (e.g., epidermal tissues and nervous system). Thus, the pluripotent cells isolated by the methods of the invention are capable of differentiating into cells of the ectoderm, endoderm, and mesoderm lineages, including neurogenic, adipogenic, cardiomyogenic, chondrogenic, myogenic and osteogenic lineages. Pluripotency of the isolated stem cells can be assessed by various in vitro and in vivo methods, including in vitro differentiation assays or in vivo teratoma formation in immunodeficient mice.

Preferably, the cells are extracted from adult neural crest tissues. Thus, the pluripotent stem cells isolated by the methods of the invention are adult pluripotent stem cells. As used herein, "adult stem cells" refer to stem cells that are not embryonic in origin nor derived from embryos or fetal tissue. The term adult stem cells also encompasses stem cells isolated from subjects of all ages (e.g. human infants and children). Tissues derived from the neural crest from which cells can be extracted include, but are not limited to, dental pulp, periodontal ligament, gut, dorsal root ganglia, exfoliated deciduous teeth (including baby teeth), hair follicle, skin, lung, cartilage, dental follicle, olfactory epithelium, turbinates (e.g., nasal concha: superior, middle and inferior), cardiac outflow tract, cardiac semilunar valves, myocardium, and cardiac septum. In certain embodiments, cells are extracted from periodontal ligament, preferably adult periodontal ligament. Methods of extracting cells from tissue samples are known to those of skill in the art and may include mechanical separation (e.g., mincing) and/or enzymatic digestion of the tissue followed by placement in appropriate culture media, such as those described herein. Cells may be optionally filtered to produce single-cell suspensions and subsequently cultured to produce clones from individual cells.

In some embodiments, the cells are extracted from tissue obtained from a patient or subject in need of treatment. In other words, the pluripotent stem cells isolated by the methods of the invention are autologous stem cells, which refers to stem cells that are derived or transferred from the same individual's body. In contrast, "allogeneic stem cells" are stem cells that are genetically different although belonging to or obtained from the same species. A patient or subject in need of treatment may be a patient or subject who has damaged organ tissue as a result of injury (e.g., spinal cord injury), ischemia (e.g. myocardial infarction or stroke), or degenerative disease (e.g. Parkinson's Disease, Alzheimer's Disease, amyotrophic lateral sclerosis, osteoarthritis, or macular degeneration). As used herein, "patient" or "subject" may encompass any vertebrate, including but not limited to, humans, primates, mammals, reptiles, amphibians and fish. However, advantageously, the patient or subject is a mammal such as a human, or a mammal such as a domesticated mammal, e.g., dog, cat, horse, and the like, or production mammal, e.g., cow, sheep, pig, and the like. In a preferred embodiment, the patient or subject is human.

In certain embodiments, cells extracted from the neural crest-derived tissue are cultured under adherent conditions. "Adherent culture conditions" involve plating cells on a substrate or surface that is optionally coated with a substance that facilitates adhesion of the cells to the substrate or surface, such as one or more components of the extracellular matrix. "Non-adherent" or "suspension" culture conditions involve growing the cells in a free-floating manner in the culture medium, e.g. in a tissue flask or container. The cells may be passaged (i.e. subcultured or split) one or more times prior to selection of cells expressing connexin 43 or other markers as described in more detail below. In some embodiments, the cells are passaged at least twice prior to selection for one or more surface markers. In other embodiments, the cells are passaged at least three times prior to selection for one or more surface markers. In still other embodiments, the cells are passaged at least four times prior to selection for one or more surface markers.

Following propagation in adherent cell cultures, cells expressing connexin 43 are selected and isolated. Connexin 43 is a surface protein that is a component of cellular gap junctions and can be detected by routine methods known to the skilled artisan. Such methods include, but are not limited to, labeling with an anti-connexin 43 antibody followed by fluorescence-activated cell sorting (FACS), magnetic bead cell sorting, or modified forms of affinity chromatography. The cells expressing connexin 43 isolated from the adherent cell culture constitute a substantially homogeneous population of pluripotent stem cells. This substantially homogeneous pluripotent stem cell population can be incorporated into pharmaceutical compositions and used in methods of tissue repair and treatment as described herein. The pluripotent stem cells positive for connexin 43 may be further expanded and propagated in culture following isolation.

In certain embodiments, the method further comprises screening the extracted or cultured cells for expression of connexin 43 or one or more stem cell markers or neural crest markers prior to isolation. Suitable stem cell markers include, but are not limited to, Oct4, Nanog, Sox2, Klf4, or combinations thereof. Neural crest markers, the expression of which may be assessed in the extracted or cultured cells, include, but are not limited to, p75 neurotrophin receptor, Nestin, Sox10, N-Cadherin, Notch1, BMP2, Slug, Snail, or combinations thereof. The cells expressing one or more stem cell or neural crest markers may be selected or isolated to obtain a subpopulation of cells that is in turn subject to selection for connexin 43 expression. Alternatively, the expression of one or more stem cell or neural crest markers may be determined in the isolated cells expressing connexin 43 to assess the homogeneity or purity of the pluripotent stem cell population. Cells that are "positive" for a marker are cells that express the marker protein at a level detectable by routine methods known to those of skill in the art, such as immunohistochemistry, FACs, immunoblotting, and the like. In contrast, cells that are "negative" for a marker refer to cells that do not express detectable levels of the marker protein using routine methods.

The present invention also includes a population of pluripotent stem cells isolated by the methods described herein. For instance, in one embodiment, the invention encompasses a homogeneous or substantially pure population of adult pluripotent stem cells, wherein said stem cells are positive for at least one stem cell marker, express connexin 43, are capable of differentiating into cells of the ectoderm, endoderm, and mesoderm lineages, and are isolated from tissue derived from the neural crest. In certain embodiments, the cells are isolated from adult periodontal ligament. In preferred embodiments, the adult pluripotent stem cells are human pluripotent stem cells and are isolated from human neural crest-derived tissue, such as adult human periodontal ligament.

As used herein, a "substantially pure population" means at least 80%, at least 85%, at least 90%, at least 95%, at least 96%, at least 97%, at least 98%, at least 99%, or 100% pure i.e., that the population comprises at least 80%, at least 85%, at least 90%, at least 95%, at least 96%, at least 97%, at least 98%, at least 99%, or 100% pluripotent stem cells. In certain embodiments, the pluripotent stem cells express one or more stem cell markers (e.g., Oct4, Nanog, Sox2, Klf4) or neural crest markers (e.g., p75 neurotrophin receptor, Nestin, Sox10, N-Cadherin, Slug) as described herein. In one particular embodiment, the pluripotent stem cells exhibit nuclear expression of Oct4. In these and related embodiments, 70% or greater, 75% or greater, 80% or greater, 85% or greater, or 90% or greater of said stem cells in the substantially pure population are positive for Oct4.

The invention also encompasses methods for preparing compositions, such as pharmaceutical compositions, including the isolated pluripotent stem cells (e.g. periodontal ligament-derived pluripotent stem cells), for instance, for use in inventive methods for repairing damaged tissue and treating degenerative disorders or conditions. In one embodiment, the pharmaceutical composition comprises a therapeutically effective amount of isolated pluripotent stem cells and a pharmaceutically acceptable carrier, wherein said isolated pluripotent stem cells are positive for at least one stem cell marker, express Connexin-43, are capable of differentiating into cells of the ectoderm, endoderm, and mesoderm lineages, and are isolated from tissue derived from the neural crest. In another embodiment, the pluripotent stem cells are isolated from human neural crest-derived tissue. In still another embodiment, the pluripotent stem cells are isolated from adult human periodontal ligament. A "therapeutically effective amount" refers to an amount sufficient to effect a beneficial or desired clinical result. For example, a therapeutically effective amount of isolated pluripotent stem cells is an amount sufficient to effect repair of damaged tissue and/or ameliorate one or more systems of a degenerative disease or disorder. In one embodiment, a therapeutically effective amount of isolated pluripotent stem cells is about $1\times10^5$ to about $1\times10^7$ cells/dose. However, the precise determination of what would be considered an effective dose may be based on factors individual to each subject, including their size, age, type of tissue damage to be repaired, and amount of time since damage, or stage/severity of disorder or disease to be treated. Thus, the skilled artisan can readily determine the dosages and the amount of isolated stem cells and optional additives, vehicles, and/or carrier in compositions to be administered in the treatment methods of the invention.

The pharmaceutical compositions comprising the isolated pluripotent stem cells can be prepared, in some embodiments, by suspending or mixing the homogeneous or substantially pure population of pluripotent stem cells as described herein with a pharmaceutically acceptable carrier. The phrase "pharmaceutically acceptable" refers to molecular entities and compositions that do not produce an adverse, allergic or other untoward reaction when administered to an animal, such as, for example, a human, as appropriate. Suitable pharmaceutically acceptable carriers include, but are not limited to, sterile water, physiological saline, glucose or the like. Standard texts, such as "REMINGTON'S PHARMACEUTICAL SCIENCE", 17th edition, 1985, incorporated herein by reference, may be consulted to prepare suitable preparations, without undue experimentation. Moreover, for animal (e.g., human) administration, it will be understood that preparations should meet sterility, pyrogenicity, general safety and purity standards as required by FDA Office of Biological Standards.

The present invention also provides methods of differentiating or preconditioning the isolated pluripotent stem cells described herein to differentiate to a particular cell lineage, such as neurogenic, adipogenic, cardiomyogenic, chondrogenic, myogenic, or osteogenic lineage. Because pluripotent stem cells have the capability of differentiating into any adult cell type, conditioning or inducing the stem cells to commit to a specific, desired cell lineage prior to administration to a patient or subject in need of treatment can minimize the in vivo generation of unwanted cell types.

A heterogeneous population of pluripotent stem cells isolated from neural crest-derived tissue (e.g. adult periodontal ligament) as described in Huang et al., 2009, which is hereby incorporated by reference in its entirety, can be used in the preconditioning or differentiation methods of the invention. Alternatively, the substantially homogeneous population of neural crest-derived pluripotent stem cells (e.g. periodontal ligament-derived pluripotent stem cells) obtained by selection of the connexin 43 surface protein as described herein can be used in the preconditioning or differentiation methods of the invention. In certain embodiments, the pluripotent stem cells are human pluripotent stem cells. Specific methods of inducing the pluripotent stem cells to differentiate into the neural and retinal lineages is described in more detail below. Methods of inducing differentiation into other lineages, including cardiomyogenic, osteogenic, and chondrogenic lineages is described in U.S. Patent Publication No. 2011/0236356, which is hereby incorporated by reference in its entirety.

In one aspect, the invention provides a method of differentiating pluripotent stem cells isolated from adult periodontal ligament to neural progenitor cells or neural cells. In one embodiment, the method comprises incubating said pluripotent stem cells in a culture media comprising epidermal growth factor (EGF) and basic fibroblast growth factor (bFGF) for a period of time, wherein a plurality of said pluripotent stem cells are differentiated into neural progenitor cells or neural cells at the end of the period of time.

The pluripotent stem cells can be cultured under adherent or non-adherent (e.g., suspension) conditions. In one particular embodiment, the stem cells are cultured under adherent conditions, for example, by plating on a substrate or surface. The stem cells may be passaged one or more times as described herein prior to exposure to the growth factors. EGF and bFGF can be added to a defined media containing inorganic salts, trace minerals, energy substrates, lipids, amino acids, vitamins, growth factors and proteins, and other components. In certain embodiments, EGF and bFGF are added to commercially available media, such as DMEM media. In such embodiments, the DMEM media may be supplemented with other components, such as nutrients (e.g., DMEM/F12 media), glucose, fetal bovine serum, penicillin, streptomycin, and antimycotics (e.g., amphotericin B). EGF may be added to the culture media at a concentration from about 10 ng/ml to about 250 ng/ml, or from about 25 ng/ml to about 150 ng/ml, or from about 10 ng/ml to about 75 ng/ml. In certain embodiments, EGF is present in a concentration of about 50 ng/ml. bFGF may be added to the culture media at a concentration from about 10 ng/ml to about 250 ng/ml, or from about 25 ng/ml to about 150 ng/ml, or from about 10 ng/ml to about 75 ng/ml. In certain embodiments, bFGF is present in a concentration of about 50 ng/ml.

To induce differentiation of or commit the isolated pluripotent stem cells to a neurogenic lineage, the stem cells should be exposed to the combination of EGF and bFGF for at least four days. The growth factor incubation period can be from about 4 days to about 12 days, or from about 6 days to about 10 days, or from about 7 days to about 21 days, or, in some embodiments, about 8 days. The incubation or exposure time may adjusted for the particular application for which the pluripotent stem cells are to be used. For instance, shorter incubation times may be desirable if the stem cells are to be preconditioned to a neurogenic lineage shortly before administration to a patient or subject in need of neuronal tissue repair. Longer incubation times may be desirable if complete or nearly complete differentiation to mature neuronal cells is required to generate, for example, ex vivo neuronal tissue for subsequent implantation as grafts.

Following the incubation period with EGF and bFGF, a plurality of said pluripotent stem cells are differentiated into neural progenitor cells or neural cells, including both neurons and glia. The differentiated cells may be identified through cell morphology, electrophysiology characteristics, and/or expression of any markers known in the art to identify the cells in question. For instance, in one embodiment, neural progenitor cells or neural cells are identified by the expression of one or more markers. Suitable markers for the identification of neural progenitor cells include, but are not limited to, nestin, MSi-1, N-cadherin, Sox1, Sox2, ABCG2, Pax6, and Tau (neurofibrillary tangle protein). Suitable markers for the identification of neurons include, but are not limited to, β-III tubulin (TUBB3; also known as Tuj1), microtubule associated proteins (e.g., MAP-1, MAP-2, and MAP-5), ChAT (choline acetyltransferase), CgA (antichromagranin A), DARRP (dopamine and cAMP-regulated phosphoprotein), DAT (dopamine transporter), GAD (glutamic acid decarboxylase), GAP (growth associated protein), NeuN (neuron-specific nuclear protein); NF (neurofilament), neurofilament medium (NEFM), NGF (nerve growth factor), γ-NSE (neuron specific enolase), SERT (serotonin transporter), synapsin, synaptophysin, Tau (neurofibrillary tangle protein), TRK (tyrosine kinase receptor; e.g., TrkA, TrkB, TrkC), TRH (tryptophan hydroxylase), TH (tyrosine hydroxylase), VRL (vanilloid receptor like protein), VGAT (vesicular GABA transporter), and VGLUT (vesicular glutamate transporter).

Glial cells include both astrocytes and oligodendrocytes. Astrocytes may be identified by expression of astrocyte markers, such as GFAP (glial fibrillary acid protein), ASTO-1, or S-100 protein. Oligodendrocytes may be identified by expression of oligodendrocyte markers, such as GC (galactocerebrocide, also referred to as GalC), MBP (myelin basic protein), CNPase (2',3'-cyclic nucleotide 3'-phosphodiesterase), NSP, RIP, MOSP, O1 or O4.

In other embodiments, the differentiated cells may be identified by cell morphology. Compact, rounded cell bodies that extend thin processes are characteristic features of neurons, whereas glial cells have flat, wide cell bodies that extend thick processes and typically have a star-like appearance (see, e.g., FIG. 12). In certain embodiments, the differentiated cells may be identified by their electrophysiological characteristics. Neural cells are electrically excitable and exhibit changes in membrane voltage mediated by activation and inactivation of voltage-gated ion channels in response to various electrical and chemical (e.g. neurotransmitters) stimuli. Typically, neurons have voltage-gated sodium and potassium channels that underlie action potentials. Thus, neuronal cells can be identified by measuring inward sodium currents and outward, delayed rectifying potassium currents by standard voltage-clamping techniques (see Example 3).

In another aspect, the invention provides a method of differentiating pluripotent stem cells isolated from adult periodontal ligament to retinal progenitor cells or retinal cells. In certain embodiments, the method comprises treating the pluripotent stem cells with a combination of an antagonist of the bone morphogenetic protein (BMP) signaling pathway and an antagonist of the WNT/beta-catenin signaling pathway. Suitable antagonists of the BMP signaling pathway include, but are not limited to, noggin, chordin, follistatin, and Xnr3. Suitable antagonists of the WNT/beta-catenin signaling pathway include, but are not limited to, Wnt Inhibitory Factor 1 (WIF1) and Dickkopf 1 (Dkk-1). In some embodiments, the method comprises treating cells with Noggin, Dkk-1, and optionally IGF-1. For instance, in one embodiment, the method comprises first obtaining neurospheres by culturing the pluripotent stem cells under non-adherent (i.e. suspension) conditions in a first induction media for a first period of time, and then plating the neurospheres on a substrate or surface in a second induction media (e.g., adherent culture) for a second period of time, wherein a plurality of said pluripotent stem cells are differentiated into retinal progenitor cells or retinal cells at the end of the second period of time in adherent culture. The stem cells may be passaged one or more times as described herein prior to the induction method (i.e., prior to the step of obtaining neurospheres).

The first induction media may comprise at least one antagonist of the BMP signaling pathway and one antagonist of the WNT/beta-catenin signaling pathway. For instance, in preferred embodiments, the first induction media comprises a first concentration of Noggin, a first concentration of Dkk-1 (Dickkopf 1), and insulin-like growth factor-1 (IGF-1). These proteins can be added to defined media, including commercially available media, as described above for the neural induction protocol. In one embodiment, Noggin, Dkk-1, and IGF-1 are added to DMEM/F12 media supplemented with B27. In some embodiments, one or more of these proteins are recombinantly produced proteins. Either the murine or human homolog of these three proteins are suitable for use in the induction media. In certain embodiments, the human homolog of the proteins are preferred. In one embodiment, mouse Noggin, human Dkk-1, and human IGF-1 are included in the first induction media.

In some embodiments, Noggin is present in the first induction media in a concentration range from about 0.5 ng/ml to about 20 ng/ml or about 1 ng/ml to about 10 ng/ml. In one embodiment, Noggin is present in the first induction media at about 1 ng/ml. Dkk-1 may also be present in the first induction media in a concentration range from about 0.5 ng/ml to about 20 ng/ml or about 1 ng/ml to about 10 ng/ml. In a particular embodiment, Dkk-1 is present in the first induction media at about 1 ng/ml. The first induction media may include IGF-1 in a concentration range of about 2.5 ng/ml to about 100 ng/ml or about 5 ng/ml to about 50 ng/ml. In certain embodiments, IGF-1 is present in the first induction media at about 5 ng/ml. In certain embodiments, the first induction media comprises 1 ng/ml Noggin, 1 ng/ml Dkk-1, and 5 ng/ml IGF-1.

Initially, the isolated pluripotent stem cells (e.g., isolated periodontal ligament-derived pluripotent stem cells) are cultured in the first induction media under non-adherent (i.e. suspension or free-floating) conditions for a first period of time to allow for formation of neurospheres. A period of about three days is generally sufficient for neurosphere formation to occur. However, the first period of time could be longer or shorter so long as neurospheres form. For instance, the first period of time may be from about two days to three weeks or from about three days to about six weeks. In addition to morphological observations, neurosphere formation can be assessed by expression of one or more neuronal progenitor cell or neural markers as described herein. For instance, in some embodiments, the neurospheres express one or more neuronal progenitor cell or neural markers selected from Nestin, p75 neurotrophin receptor, ABCG2, Pax6, and TUBB3 (also known as Tuj1).

Following neurosphere formation, the neurospheres are plated on a substrate or surface (i.e. under adherent conditions) in a second induction media for a second period of time. Suitable substrates or surfaces for neurosphere plating include, but are not limited to, glass coverslips and microtiter wells or sheets produced with any of the following materials: controlled pore glass, functionalized glass, ceramics, silica, silica-based materials, polystyrene, polystyrene latex, polyvinyl chloride, polyvinylidene fluoride, polyvinyl acetate, polyvinyl pyrrolidone, polyacrylonitrile, polyacrylamide, polymethyl methacrylate, polytetrafluoroethylene, polyethylene, polypropylene, and polycarbonate, divinylbenzene styrene-based polymers, celluloses (such as nitrocellulose), cellulosic polymers, polysaccharides, and metals. The substrate or surface may be coated with a substance to facilitate adhesion, such as one or more components of the extracellular matrix, including collagen IV, fibronectin, laminin, and vitronectin. In certain embodiments, the substrate or surface is coated with matrigel. Matrigel is a gelatinous protein mixture secreted by mouse tumor cells and is commercially available (BD Biosciences, New Jersey, USA). The mixture resembles the complex extracellular environment found in many tissues.

The second induction media typically comprises a combination of an antagonist of the BMP signaling pathway and one antagonist of the WNT/beta-catenin signaling pathway. The antagonists can be the same or different than the antagonists present in the first induction media. In embodiments in which the antagonists are the same as the antagonists in the first induction media, the antagonists in the second induction media are present in a higher concentration. In certain embodiments, the second induction media comprises a second concentration of Noggin and a second concentration of Dkk-1, and optionally IGF-1. Similar to preparation of the first induction media, Noggin and Dkk-1 can be added to a defined media, such as DMEM/F12 media. In such embodiments, the media may further comprise N2 supplement (Invitrogen). The second concentration of Noggin may be ten-fold higher than the first concentration of Noggin. Thus, Noggin may be present in the second induction media in a concentration range of about 5 ng/ml to about 200 ng/ml or about 10 ng/ml to about 100 ng/ml. In one embodiment, Noggin is present in the second induction media at about 10 ng/ml. Similarly, the second concentration of Dkk-1 may be ten-fold higher than the first concentration of Dkk-1. Thus, Dkk-1 may be present in the second induction media in a concentration range of about 5 ng/ml to about 200 ng/ml or about 10 ng/ml to about 100 ng/ml. In one embodiment, Dkk-1 is present in the second induction media at about 10 ng/ml. IGF-1 may optionally be present in the second induction media at the same range of concentrations as described for the first induction media. In certain embodiments, the second induction medium comprises 10 ng/ml of Noggin, 10 ng/ml of Dkk-1, and optionally 5 ng/ml IGF-1.

The second period of time should be of sufficient length to allow the neurospheres to attach to the substrate and the cells to expand out from the neurosphere. Thus, the second period of time should be at least 7 days and can extend to 45 days or more. For instance, the second period of time is about 7 days to about 50 days. In some embodiments, the second period of time is at least 25 days.

Following the adherent culture in the second induction media (i.e. at the end of second period of time), a plurality of said pluripotent stem cells are differentiated into retinal progenitor cells or retinal cells. The differentiated cells may be identified through expression of one or more markers of retinal development. For instance, in some embodiments, a plurality of the retinal progenitor cells or retinal cells express one or more eye field specification genes, including without limitation Lhx2, DCX, Chx10, Rx, Sox2, and Otx2. In related embodiments, a plurality of the retinal progenitor cells or retinal cells are $Pax6^{nuclear}$ and Rx positive—that is, express Rx in combination with nuclear expression of Pax6. In other embodiments, a plurality of the retinal progenitor cells or retinal cells may express one or more markers of photoreceptors, such as Nrl (Nrl), rhodopsin, and/or rhodopsin kinase. The photoreceptor phenotype may also be identified by functional assays, such as increases in intracellular calcium induced by glutamate stimulation using standard calcium imaging techniques. Thus, in some embodiments, a plurality of the retinal progenitor cells or retinal cells exhibit an increase in intracellular calcium in response to glutamate stimulation as compared to baseline cellular calcium levels (i.e. in the absence of glutamate).

The isolated pluripotent stem cells and compositions comprising such stem cells can be used in various therapeutic and regenerative medicine applications. For instance, in one embodiment, the present invention provides a method of repairing damaged tissue in a subject in need thereof by administering to the subject an isolated population of pluripotent stem cells or pharmaceutical compositions comprising such cells as described herein. The isolated pluripotent stem cells, such as the connexin 43 positive stem cells, are suitable for use in the therapeutic methods and may optionally be preconditioned or induced to differentiate into specific cell lineages according to the induction methods described herein. In preferred embodiments, the pluripotent stem cells are obtained from the same patient or subject to whom the cells are to be administered (i.e. the pluripotent stem cells are autologous).

Because the pluripotent stem cells of the invention have the ability to differentiate into cells of all three germ layers (endoderm, mesoderm, and ectoderm), including neurogenic, adipogenic, cardiomyogenic, chondrogenic, myogenic and osteogenic lineages, any type of damaged tissue may be repaired by administration or implantation of the pluripotent stem cells (e.g. periodontal ligament-derived pluripotent stem cells). For instance, in certain embodiments, the damaged tissue is neural tissue, retinal tissue, cardiac tissue, skeletal muscle tissue, bone, or cartilage. The damaged tissue may arise from some type of injury (e.g., a mechanical muscle, ligament, or bone injury or spinal cord compression or transaction), an ischemic event (e.g., myocardial infarction or stroke), or degenerative disease or condition (e.g., Alzheimer's disease, Parkinson's disease, amyotrophic lateral sclerosis, osteoarthritis, macular degeneration).

In certain embodiments, the damaged tissue is neural tissue. Accordingly, the invention includes a method of treating neurodegenerative disorders and brain (e.g. stroke) and spinal cord injuries comprising administering to the subject an isolated pluripotent stem cell population as described herein. In one embodiment, the isolated pluripotent stem cell population is induced to differentiate into a neurogenic lineage by exposure to EGF and bFGF according to the methods described herein prior to administration of the stem cells to the patient or subject.

In other embodiments, the damaged tissue is retinal tissue. Accordingly, the invention also includes a method of treating ocular diseases by administering to the subject an isolated pluripotent stem cell population as described herein. In one embodiment, the isolated pluripotent stem cell population is induced to differentiate into a retinal progenitor cell/retinal cell lineage using the two step induction protocol described herein prior to administration of the stem cells to the subject. Ocular diseases that may be treated by such a method include, but are not limited to, retinitis pigmentosa, age-related macular degeneration (exudative and non-exudative), glaucoma and diabetic retinopathy.

Administration of the isolated pluripotent stem cells (e.g., periodontal ligament-derived pluripotent stem cells) or compositions thereof to a patient or subject for therapeutic purposes will be via any common route so long as the target tissue is available via that route. This includes administration by systemic or parenteral methods including intravenous injection, intraspinal injection, intrathecal injection, or intracerebral, intraocular, intravitreal, intra-articular, intradermal, subcutaneous, intramuscular, or intraperitoneal methods. The pluripotent stem cells may also be administered to a patient or subject in need of treatment by implantation of a tissue graft comprised of the stem cells or differentiated cells generated from the stem cells. Such tissue grafts can be produced ex vivo by differentiating the pluripotent stem cells in culture using the media and differentiation methods described herein or described in U.S. Patent Publication No. 2011/0236356, which is hereby incorporated by reference in its entirety.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1. Isolation of Pluripotent Stem Cells from Adult Human Periodontal Ligament Recently, our laboratory reported that a population of cells within the periodontal ligament of adult humans retained some expression of embryonic and pluripotency-associated markers, as well as neural crest-specific markers (Huang et al., 2009). The objective of this example was to investigate whether connexin 43 (Cx43) could be used as a selection marker to isolate a substantially homogeneous, pluripotent periodontal ligament-derived stem cell population.

Impacted 3rd molars were obtained from healthy human donors following routine medical procedures requiring their extraction and the middle third of the periodontal ligament was enzymatically digested in a collagenase solution overnight and filtered through a 40 μm cell strainer to obtain single-cell suspensions. Cells were then selected for adherent-dependence and cultured in Dulbecco's Modified Eagle Medium (DMEM; Invitrogen) supplemented with 10% Fetal Bovine Serum (Invitrogen), and 100 U/ml Penicillin-streptomycin (Invitrogen) and 0.1% v/v amphotericin B. Passaging of the cells was achieved by enzymatic digestion in Trypsin/EDTA (Invitrogen) and subcultured as mentioned above. Cell lines were passaged at least twice before selection of Cx43+ fraction was performed.

Figure 2:
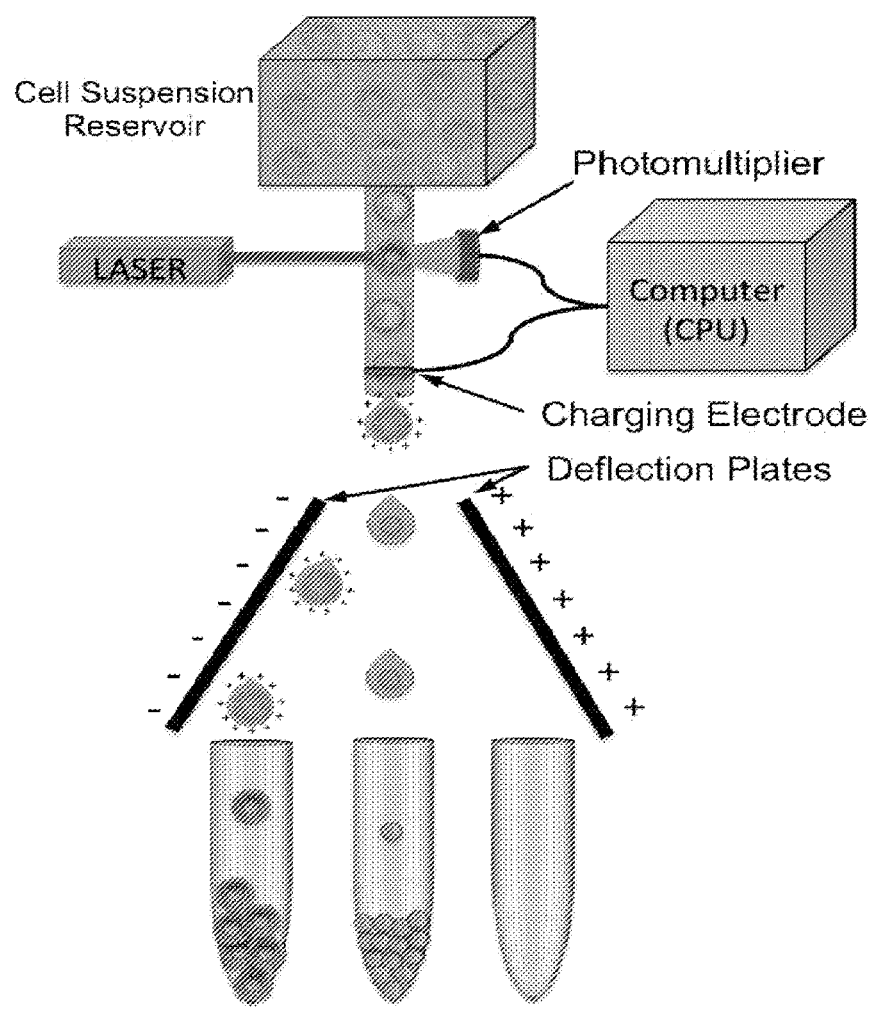
FIG. 2. Diagram illustrating the FACS technique Immunocytochemically-positive marked cells are detected by the photomultiplier and loaded in electrically charged droplets which get deflected by the deflection plates and collected separately from negative cell populations.

For Cx43 selection, all cells were used at either passage 3 or 4. Following enzymatic lifting, the cells were maintained at 4° C. and incubated in primary antibody against human connexin-43 (abcam #ab11370) diluted to 1:100 in 2% FBS-containing DMEM overnight with constant agitation. Following primary antibody incubation, cells were lightly centrifuged at 1,000 rpm for 10 minutes, washed with PBS twice and then marked for magnetic (FIG. 1) or fluorescence-activated sorting (FIG. 2). For magnetic sorting, following primary antibody incubation and wash, cells were incubated in pre-washed Dynabeads® conjugated with sheep anti rabbit IgG secondary antibody (Invitrogen, #112-03D) according to the manufacturers recommended protocol for 4 hours at 4° C. The cell-bead suspension was then placed on a magnetic tube rack and allowed to settle for 2 minutes, after which the supernate was carefully removed without disturbing the cell-bead conjugates aggregated towards the magnet. Cell-bead suspension was washed twice in PBS following the magnetic aggregation procedure described above and then resuspended in culture media and seeded onto adherent culture flasks. Cells were then allowed to adhere for a period of 3 days and washed several times with PBS to remove excess magnetic beads still remaining in culture.

Figure 3:
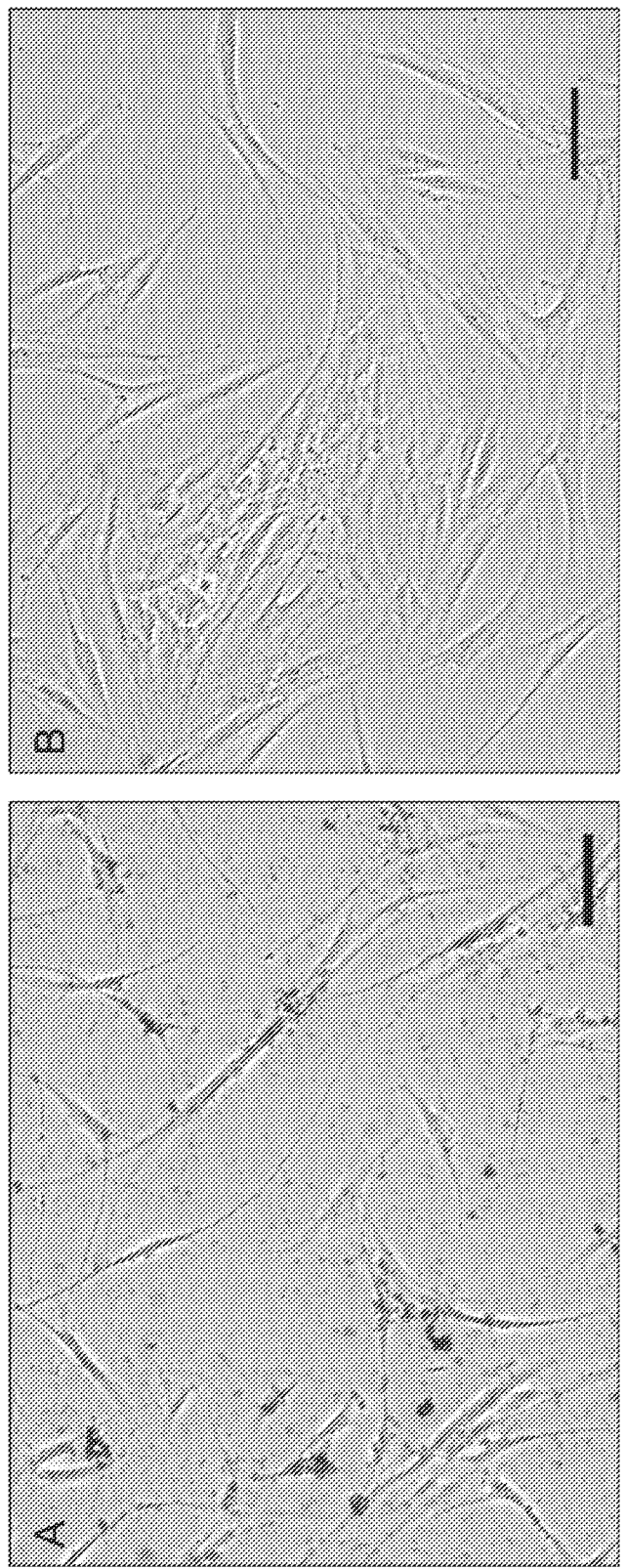
FIG. 3. Brightfield images of cell culture of Cx43+ (with remaining magnetic beads) (A), and Cx43-negative (B) periodontal ligament-derived stem cells. Bar=50 μm.
Figure 4:
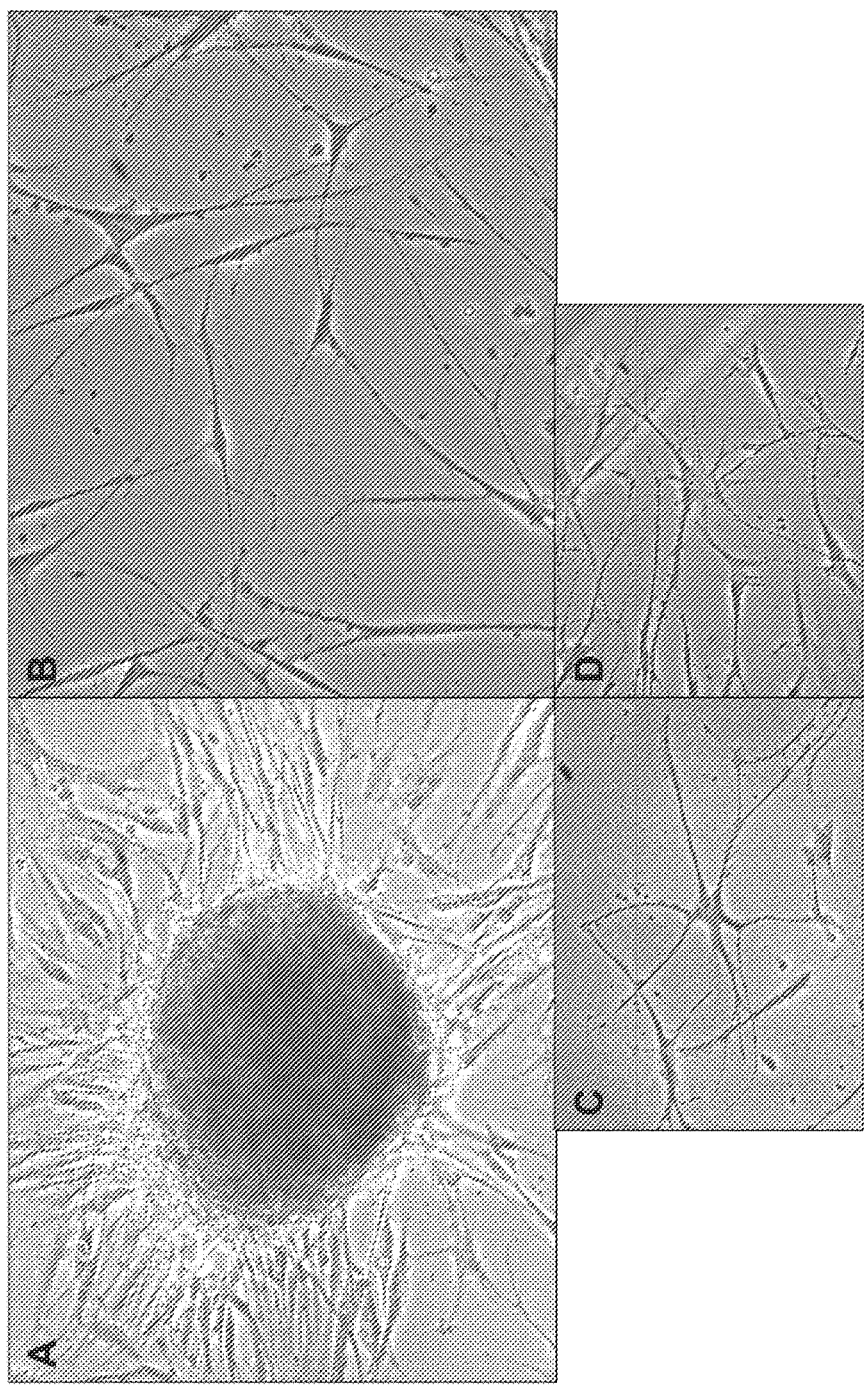
FIG. 4. Brightfield images of Cx43+ periodontal ligament-derived stem cell culture following non-adherent aggregation and subsequent adherent culture. (A) Cell cluster from aggregation stage attached to culture surface. (B) Representative image of branched network culture morphology. (C-D) Observed neural-like phenotypes in aggregate-adherent cultures.

Magnetic bead selection (FIG. 1) of Cx43+ periodontal ligament-derived stem cells (PDLSC) yielded a number of cells presenting the correct membrane conformation of the gap junction protein as can be seen by the covering of the cell body with the iron beads immediately after selection (FIG. 1, panel 4 image) and remaining after establishment of adherent cultures (FIG. 3A). Cultured Cx43+ cells grown in adherent culture appeared similar to fibroblastic-like or other mesenchymal cells. Morphologically, however, these cells appeared to be thinner, and elongate beyond the traditional spindle-like shape of fibroblastic cultures, with fairly long processes (some >1 mm) that afforded them a more neural-like appearance (FIG. 3A). Conversely, Cx43-negative fractions had a complete fibroblastic-like appearance and were flatter and much wider than their Cx43+ counterparts (FIG. 3B). Furthermore, when grown in non-adherent conditions, the Cx43+ cells readily aggregated into what could be described as neurosphere-like structures (FIG. 4A), which then created highly branched networks when allowed to adhere (FIG. 4B). Within these cultures, several neural-like morphologies could be observed including glial and neuron-like structures (FIG. 4C-D).

Figure 5:
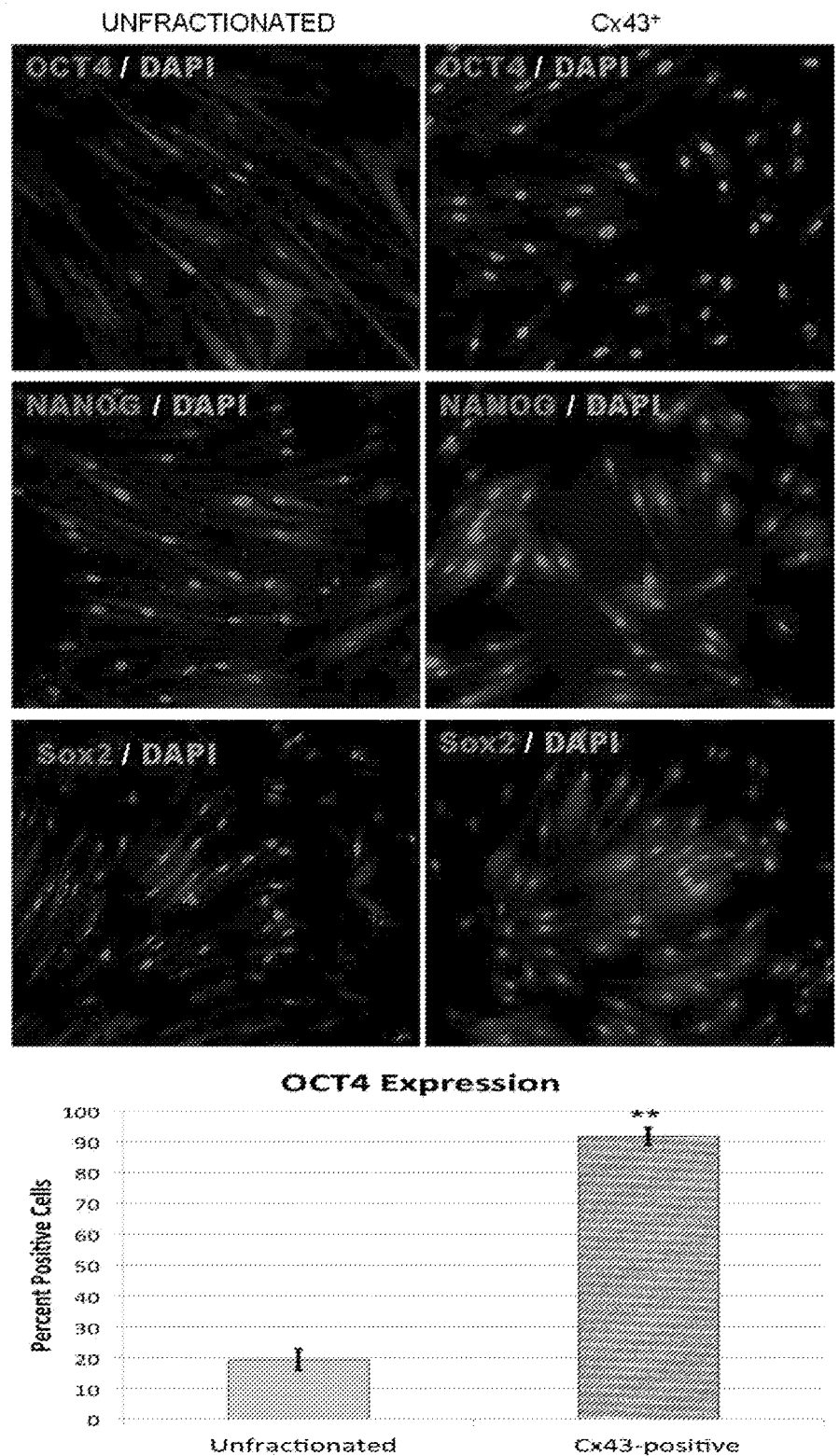
FIG. 5. Double immunohistochemical images (top) of the expression of pluripotency-associated transcription factors OCT4, Nanog, and Sox2 (red) and nucleic acids (blue) in unfractionated (left) and Cx43+ (right) cell populations of periodontal ligament-derived stem cells. Bar graph (bottom) depicting the quantitative expression of transcription factor OCT4 in unfractionated and Cx43+ cell populations of periodontal ligament-derived stem cells. (**$p<0.01$). Images are representative of obtained results for three cell lines.

Immunohistochemical analysis for the expression of pluripotency-associated markers OCT4, Nanog, and Sox2 revealed that Cx43+ selection augmented the percentage of cells staining positive for these markers when compared to that seen in heterogeneous cultures of PDLSC as previously reported by our group (Huang et al., 2009). For the expression of transcription factor OCT4, FIG. 5 clearly shows that Cx43+ selection enriched not only the percentage of positively marked cells (19.46%±3.40 for heterogeneous cultures vs. 91.76%±2.81 for Cx43+ cells; **p<0.01), but also the presentation of this marker within these cultures. Heterogeneous cultures of PDLSC had several positively marked cells for OCT4; however, most of the staining was not located within the nucleus of the cell, but in the peri-nuclear region—possibly at translational sites for the protein. Conversely, once the cell population was enriched to a homogeneous Cx43+ phenotype, OCT4 expression was observed mainly in the cell nucleus with positive staining still observed at peri-nuclear regions of some of the cells. Although not as significant as for OCT4, the selection of Cx43+ cells had a similar augmenting effect on the level of expression and pattern of presentation of Nanog and Sox2 (FIG. 5). Although both Nanog and Sox2 were originally seen in the heterogeneous cultures of PDLSCs, their expression and nuclear translocation was much more pronounced (in intensity and number) when the cells were enriched to a homogeneous Cx43+ phenotype (FIG. 5).

Figure 6:
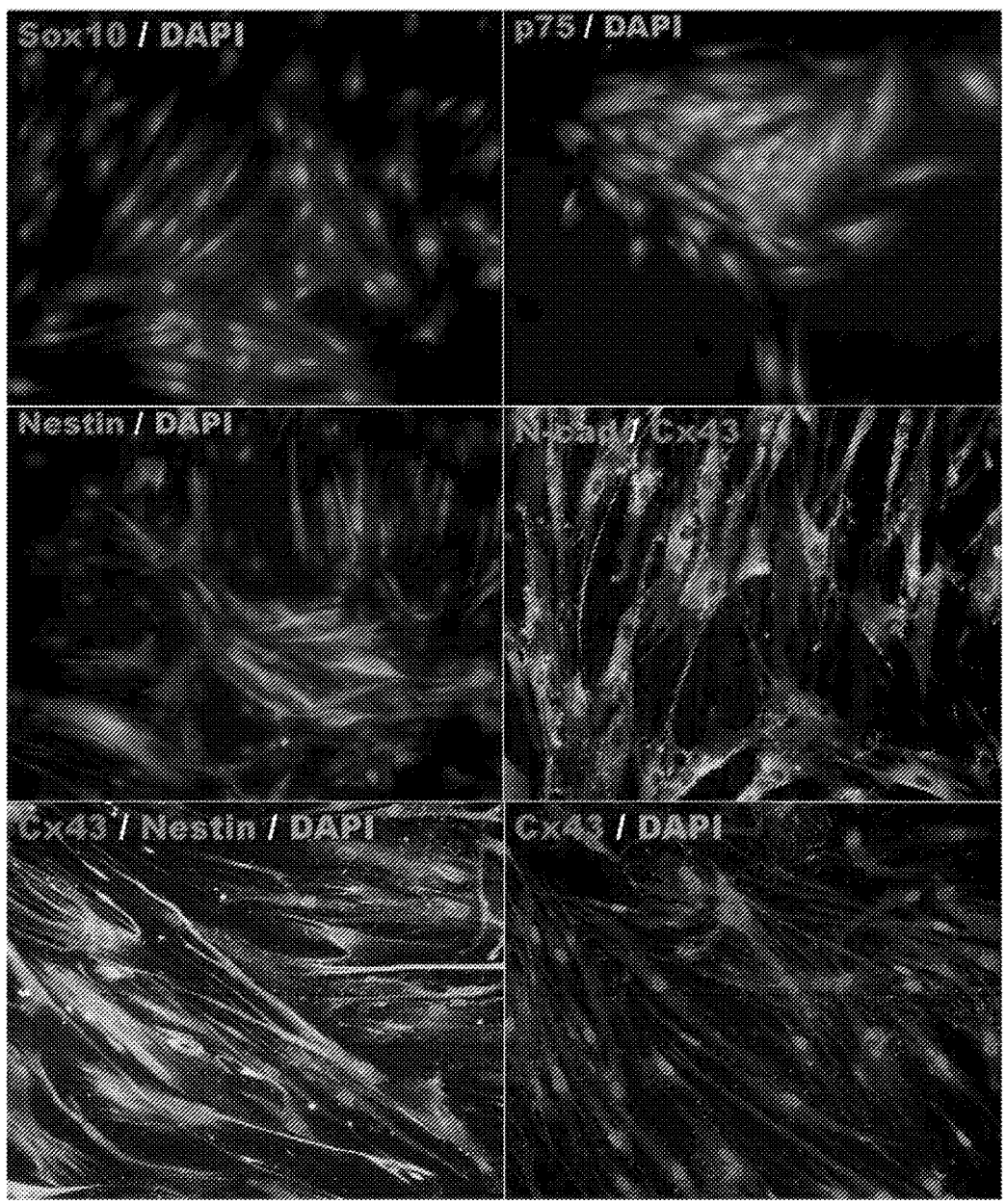
FIG. 6. Immunohistochemical images of the expression of neural crest-specific markers Sox10, p75NTR, Nestin, and N-cadherin (N-cad) in Cx43+ cell populations of periodontal ligament-derived stem cells. Middle right and bottom left images show co-expression and localization of N-cadherin and Nestin, respectively, with Cx43 in these cells. Images are representative of obtained results for three cell lines.

Connexin 43+ cultures were positive for the neural crest-specific transcriptional factor Sox10 (FIG. 6), a known neural crest specifier gene (Bronner, 2012). Similarly, the selected cells were positive for the expression of the p75 neurotrophin receptor (p75NTR), another marker recently proposed to isolate neural crest-derived stem cells (Wen et al., 2012). Analysis of the correlation between Cx43 expression and the neural marker nestin, as well as the neural crest modulator N-cadherin (Xu et al., 2001), revealed that nearly all cells ubiquitously expressed both markers as clusters on cell membranes and within cell bodies (FIG. 6). Furthermore, Cx43 immunohistochemical analysis showed that selected cells express this gap junction protein as discrete membrane-bound structures specifically at cell-cell interfaces, indicating the correct functional presentation of the protein within these cells.

The results of the experiments described in this example show that enrichment through Cx43+ marker expression had a profound effect on the phenotypic expression of pluripotency-associated markers OCT4, Nanog, and Sox2. Cx43+ cells have a significantly greater number of OCT4 positive cells than the unfractionated cell population from the same donors. Moreover, Cx43+ cells presented a functional expression of these markers with nuclear translocation of all 3 markers seen mainly in Cx43+ cells (FIG. 5). Thus, Cx43 is a useful selection marker for the isolation of pluripotent stem cells in the adult periodontal ligament and may also be a useful selection marker for remnant neural crest stem cells in other tissues derived from this embryological structure.

Methods

For immunohistochemical analysis, Cx43+ selected cells were grown on poly-1-lysine coated glass coverslips at a density of 2,500 cells/cm$^2$ and allowed to reach confluence. Cells were then fixed in 10% neutral buffered formalin for 10 minutes at room temperature. Samples were then washed 3 times in PBS containing 0.05% v/v Tween 20 (Sigma). For nuclear marker staining, further incubation for 10 min in 0.1% Triton X-100 was performed. All samples were then blocked using 5% BSA (containing 0.05% Tween 20) in PBS for 1 hour at room temperature. Samples were then incubated in primary antibody (Rabbit pAb to OCT4, Nanog or Sox2) diluted to 1:200 in blocking buffer overnight at 4° C. Following incubation with primary antibodies, the samples were washed twice in PBS and then incubated in secondary antibody (Bovine anti Rabbit IgG-TRITC) at a 1:200 dilution for 2 hours at room temperature. To confirm the neural crest origin of the cells, primary antibodies against Sox10, p75, N-cadherin and Nestin were used. N-cadherin and Nestin expression was correlated with the Cx43 expression in the cells using the same protocol as described above (dilution: 1:200). All antibodies were purchased from either Abcam (Abeam, Cambridge Mass.) or Santa Cruz Biotechnology (Santa Cruz Calif.). Samples were finally washed twice in PBS, mounted in VectaShield with DAPI (Vector Labs, Burlingame Calif.) and imaged using a Nikon Eclipse Ti inverted fluorescent microscope. Unsorted, heterogeneous cultures of PDL cells were maintained as controls for comparison. Quantitative expression levels of OCT4 were determined by the number of positively marked cells versus total number of nuclei in frame of view for both heterogeneous and Cx43+ cells for several frames of view (n=8).

All numerical values presented reflect mean±standard deviation. Statistical analyses were performed by means of two-tailed student t-tests and statistical significance was determined by any statistical test returning a p value less than 0.05 (p<0.05).

Example 2. Connexin 43-Positive Periodontal Ligament-Derived Stem Cells Form Teratomas with Mature Structures In-Vivo To determine whether Cx43$^+$ periodontal ligament-derived stem cells (PDLSCs) were truly pluripotent and could generate cell types from all three embryological germ layers (ectoderm, mesoderm, and endoderm), immunodeficient mice were inoculated with Cx43+ PDLSCs obtained by the method described in Example 1 in air capsules created in the lateral flank of the kidneys and testis. Inoculated mice generated neoplastic tumor growth in all injection sites (FIG. 7F). Teratoma tissues consisted of scattered regions of differentiated cells containing tissues from all three embryological germ layers clearly identifiable. Among the tissues identified were cartilage and ossified cartilage (mesoderm, FIGS. 7A-B), glandular and duct structures (endoderm, FIGS. 7C-D), and pigmented cells (ectoderm, FIG. 7E).

Closer histological analysis of teratoma tissues also revealed the presence of mature structures including double-walled eccrine sweat glands (FIG. 8A), gut epithelium with enterochromaffin cells (FIG. 8B), and smooth muscle (FIG. 8C). Immunohistochemical analysis of obtained tissues confirmed these observations (FIGS. 8E-G) and also showed the existence of glial cells within defined pockets of teratoma tissues (FIGS. 8F1-2) that stained positive for glial fibrillary acidic protein (GFAP). Finally, immunohistochemical analysis demonstrated that there are regions of undifferentiated stem cells still expressing the transcriptional factor OCT4 (FIG. 8D1-3).

Figure 7:
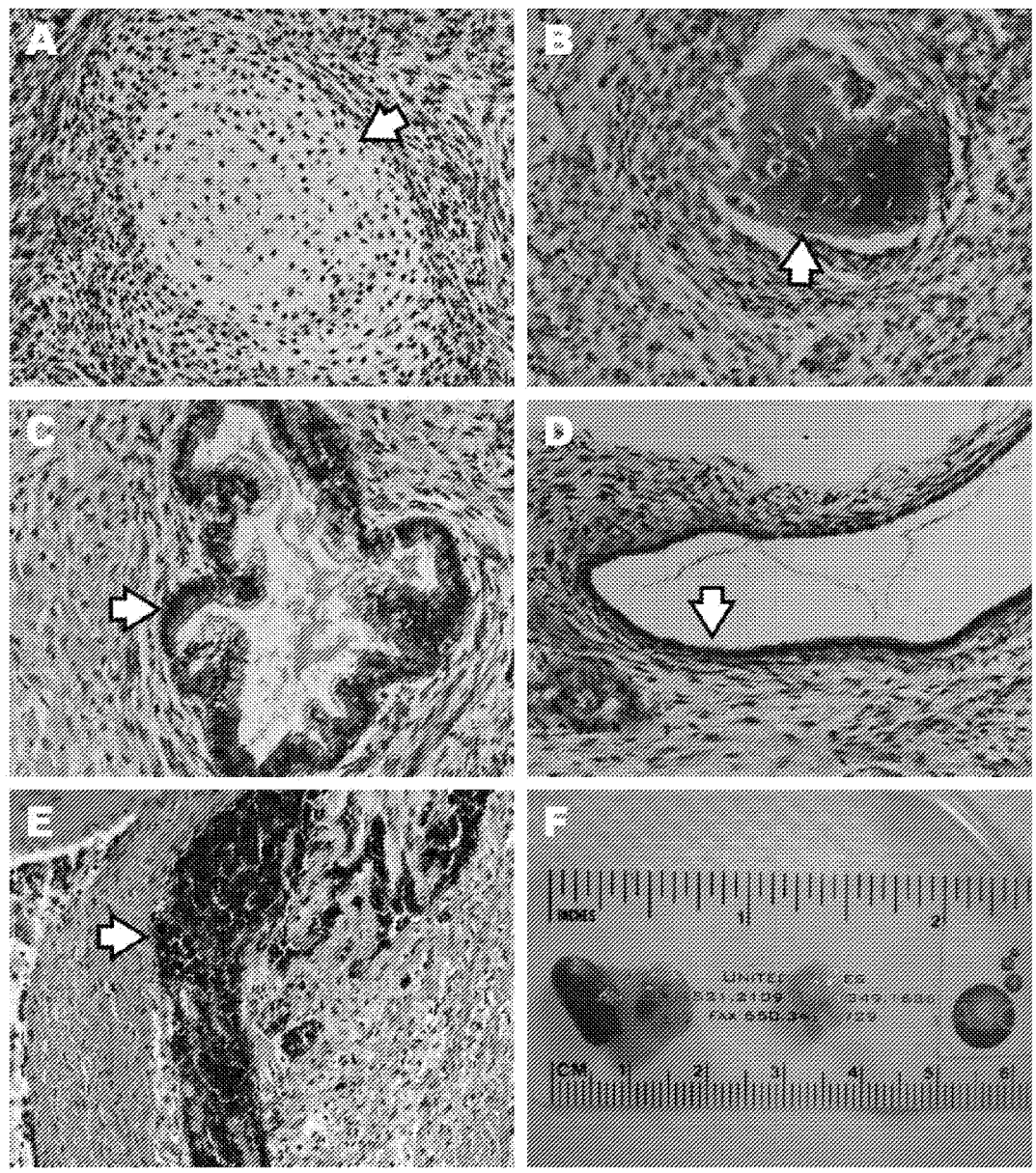
FIG. 7. Hematoxilin and Eosin (H&E) stained histological section images of identified tissues within teratomas formed by Cx43M19p5 cell line (Cx43+ periodontal ligament-derived stem cells) in immunodeficient mice. Images show mesodermal [cartilage (A), ossified cartilage (B)], endodermal [glands (C), ducts (D)], and ectodermal [pigmented cells (E)] within the tumor mass. Image F is a representative image of tumors formed on kidneys (left) and testis (right) of cell-inoculated animals.
Figure 8:
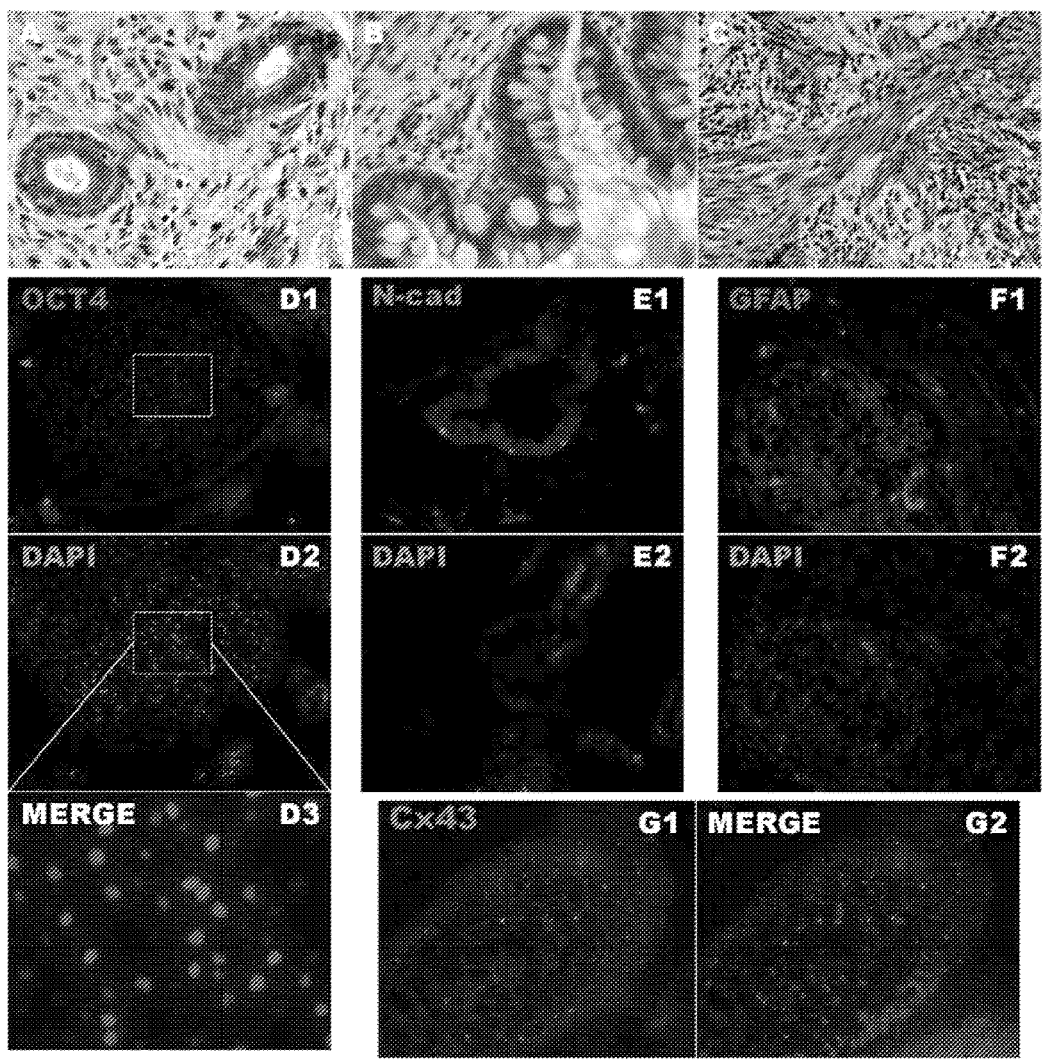
FIG. 8. Top: Hematoxilin and Eosin (H&E) stained histological section images of identified neural crest-associated tissues within teratomas formed by Cx43M19p5 cell line (Cx43+ periodontal ligament-derived stem cells) in immunodeficient mice. Images show formation of mature human eccrine sweat glands (A), intestinal epithelium (B) and smooth muscle (C) tissues within teratoma masses. Bottom: Immunohistochemical images showing undifferentiated stem cells expressing OCT4 (D1-3), as well as positively marked endoderm (E1-2) and ectoderm (F1-2). Cells expressing connexin 43 were found in structures similar to those where GFAP neural marker was localized (G).

The results of this experiment show that, in an in-vivo setting, Cx43+ PDLSCs were capable of generating teratomas in 100% of the inoculation sites. The obtained teratoma tissues contained clearly identifiable mature structures from all of the three germ layers (FIGS. 7 and 8). This observation was further confirmed by immunohistochemical analysis of tumor sections showing expression of glial marker GFAP (FIG. 8F), and endodermal marker N-cadherin (FIG. 8E). The neural crest origin of these cells was demonstrated by the expression of several neural crest markers. Specifically, the expression of transcription factor Sox10 and membrane marker p75 provide evidence of the neural crest origin of the isolated stem cell population (see Example 1). Furthermore, the identification of eccrine sweat glands (FIG. 8A), mature gut epithelium containing enterochromaffin cells (FIG. 8B), and glial cells (FIG. 8F) in teratomas formed by Cx43+ PDLSCs further confirms these cells as remnant neural crest stem cells. The presence of the double-walled eccrine sweat glands in teratoma tissue confirms the human origin of the tumor cells, since murine skin does not possess endogenous sweat glands and those found in the palmar skin of mice are single-cell walled type glands (Nejsum et al., 2005). These observations confirm that Cx43+ PDLSCs are a remnant neural crest-derived pluripotent stem cell population that can be isolated from adult neural crest tissues, such as the periodontal ligament.

Methods

Following isolation of Connexin 43+ cell fraction as described in Example 1, a teratoma formation service and analysis was performed by Applied StemCell Inc, (Fremont, Calif.). Cells provided to Applied StemCell, Inc were from the cell line Cx43M19 at passage 5. By means of a novel kidney and testis capsule injection technique, 1.5-2 million cells in 30% matrigel (BD Biosciences) were injected into an air capsule created in the lateral flank of the kidneys and testis (3 sites of injection in each) under anesthesia, sutured closed and allowed to reach homeostasis. Mice used were Fox Chase SCID-beige, male, 6 week old mice (Charles Rivers) and a total of three mice were used for the procedure. The animals were sacrificed 88 days post-injection of the cells and solid tumors were fixed in 10% formalin overnight, embedded in paraffin, cut into 5-µm serial sections, and processed for hematoxylin and eosin (H&E) staining. Pathological assessments were performed by the contracted company with following assessments of provided tissue sections performed by collaborating pathologists in our institution.

Example 3. Neural Induction of Adult Human Periodontal Ligament-Derived Stem Cells Stem cells in the body differentiate into several cell types based on various environmental cues, and studies have shown that neural-like and glial-like cells have been successfully generated from multiple (human and animal) stem cells (Kim and de Vellis, 2009), including induced pluripotent stem cells (iPSCs) (Kuo and Chang, 2012; Kuo and Wang, 2012), embryonic stem cells (ESCs) (Ostrakhovitch et al., 2012), mesenchymal stem cells (MSCs) (Cardozo et al., 2012), and neural stem cells (Ribeiro et al., 2012; Ostrakhovitch et al., 2012). MSCs, the most widely studied stem cell type, have undergone several protocols for generating neural-like cells. Recent methods for inducing MSCs (human and animal) to neural-like cells in vitro have included: chemical and growth factors (Jang et al., 2010; Qian et al., 2010; Cheng et al., 2009; Li et al., 2009), microRNA techniques (Zhou et al., 2012), and growing on different biomaterial/extracellular matrix surfaces (D'Angelo et al., 2010; Mruthyunjaya et al., 2010). Even if not able to generate "fully functioning" tissues or organs in vitro, pre-committing stem cells to various lineages is important in order to prevent undesired cell types in vivo.

Pluripotent periodontal ligament-derived stem cells (PDLSC) express neural crest markers and can differentiate into ectoderm, mesoderm, and endoderm lineages (see Examples 1 and 2). As both PDLSCs and many neural types are derived from the neural crest, the stem cells of the periodontal ligament are more closely related to neural cells than other types of stem cells. Therefore, the objective of this example was to determine if neural-like cells could be generated from PDLSCs by exposing the cells to a combination of epidermal growth factor (EGF) and basic fibroblast growth factor (bFGF).

PDLSCs were harvested from impacted wisdom teeth as previously described (Example 1; Huang et al., 2009). Cells were cultured with HGCCM and passaged when they reached ~70% confluence. HGCCM medium consisted of high glucose Dulbecco's modified eagle medium (DMEM) supplemented with 10% fetal bovine serum (FBS), 1% penicillin streptomycin (100 units/ml Penicillin and 100 µg/ml Streptomycin) and 0.1% amphotericin B (0.25 µg/ml). Cells that were passage 4 were used for all of the experiments. PDLSCs were separated into two groups: control and EGF+bFGF treated. All cells were plated at a density of 4000 cells/well in 6-well tissue culture plastic plates. All cells were plated using HGCCM. Cells were allowed to adhere to the plates overnight. Media was removed the following day and treatments were begun. The control cells were cultured in HGCCM for the duration of the experiment. EGF and bFGF were each added to the EGF+bFGF treated group at a concentration of 50 ng/ml. Media was changed every 2 days for a total of 8 days of treatment. Cells were then collected for RNA extraction or fixed for immunohistochemical staining.

Gene Expression

Figure 9:
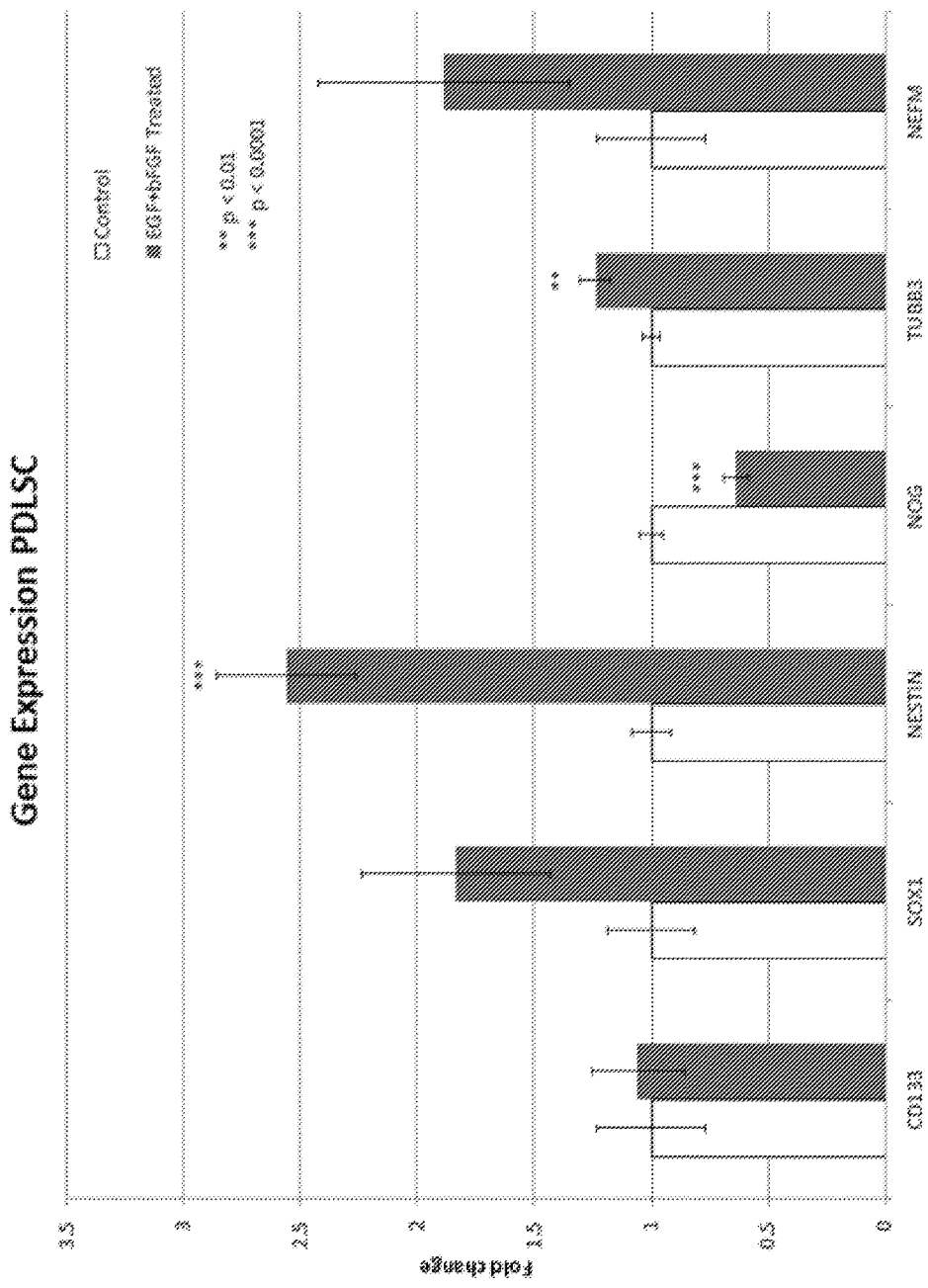
FIG. 9. Gene expression of PDLSC following EGF+bFGF Treatment. A significant increase can be seen in key immature neuron/progenitor markers following EGF+bFGF treatment (TUBB3 $p<0.01$, NESTIN $p<0.0001$). A significant decrease is also seen in NOG ($p<0.0001$). Data was pooled from 3 separate experiments. Control n=12, Treated n=18.

Following treatment with EGF+bFGF, several genetic marker categories were examined with qPCR to determine changes in the genotypes of the cells: adult/neural stem cell (CD133, SOX1, noggin (NOG)), neural progenitor/immature neuron (β-III tubulin (TUBB3) and nestin), and mature neuron (neurofilament medium (NEFM)). The genes and associated primers used in the qPCR analysis are shown in Table 1 below. Genetic analysis demonstrated significant changes in gene expression of several key genes following treatment with EGF+bFGF (FIG. 9). In particular, there was a statistically significant increase in the expression of the neural progenitor/immature neuron markers nestin and TUBB3. SOX1, one of the neural stem cell genes, showed a marked increase in expression, along with NEFM, a mature neuron marker. Interestingly, the expression of NOG significantly decreased following the induction protocol. Taken together, the results from the gene expression suggest that the induction protocol (treatment with EGF+bFGF) induces a switch in the PDLSCs from a multipotent state to a neural lineage.

TABLE 1

Genes and associated primers for qPCR analysis

| Gene | Accession Number | Forward Primer | Reverse Primer |
|---|---|---|---|
| CD133 | NM_006017.1 | GATGCCTCTGGTGGGGTATTTC (SEQ ID NO: 1) | TTTCCTTCTGTCGCTGGTGC (SEQ ID NO: 2) |
| SOX1 | NM_005986 | TGCTGGATTCTCACACAC (SEQ ID NO: 3) | CTCGTCAGGAATAATGAACAAG (SEQ ID NO: 4) |
| Nestin (NES) | NM_006617.1 | ATCAGATGACATTAAGAC (SEQ ID NO: 5) | CTTCAGTGATTCTAGGAT (SEQ ID NO: 6) |
| Noggin (NOG) | NM_005450 | AACTGTGTAGGAATGTATATGTG (SEQ ID NO: 7) | ATTAGCAACAACCAGAATAAGT (SEQ ID NO: 8) |
| β-tubulin III (TUBB3) | NM_006086 | CAAGTTCTGGGAAGTCATCA (SEQ ID NO: 9) | TTGTAGTAGACGCTGATCC (SEQ ID NO: 10) |
| Neurofilament Medium (NEFM) | NG_008388 | TTGGCAAGGGAAACAAACAC (SEQ ID NO: 11) | TCAGGGAAATTGGGATGTATATGT (SEQ ID NO: 12) |

Scanning Electron Microscopy and Immunohistochemistry

Figure 10:
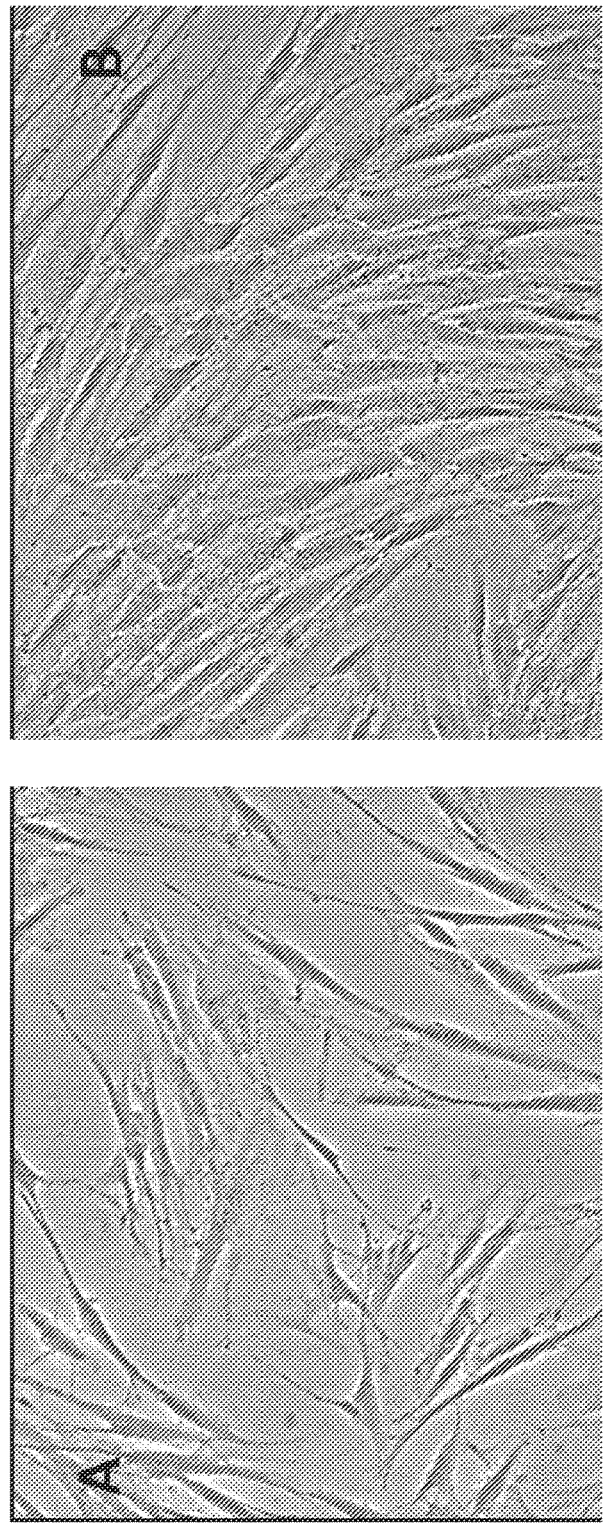
FIG. 10. Light microscopic images of (A) EGF+bFGF-treated PDLSCs and (B) untreated, control PDLSCs. The treated cells (A) connect and begin to form networks, whereas the untreated, control cells (B) coalesce and form no visible cell-cell connections.
Figure 11:
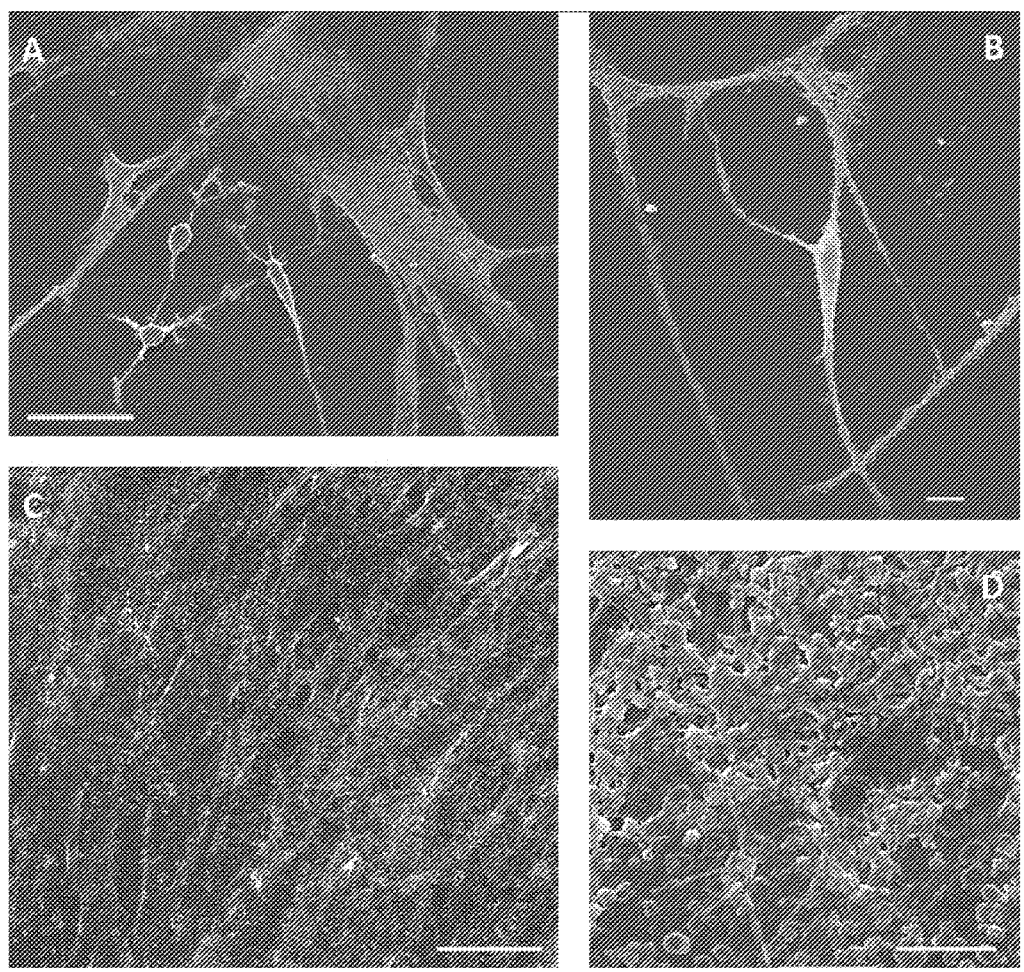
FIG. 11. Scanning Electron Micrographs of EGF+bFGF-treated PDLSCs and untreated, control PDLSCs. (A) Treated PDLSCs have two distinct phenotypes. The glial phenotype is wide and flat, with thick processes. The neuronal phenotype is characterized by a more rounded and raised cell body, with thin processes that then have further branching. Scale bar=50 μm. (B) The treatment induces a neuronal phenotype with a raised cell body, with thin processes, which connect to processes from other cells. Scale bar=10 μm. (C) Untreated, control PDLSCs have no visible processes, and form a "sheet" of cells instead of a cell network. Scale bar=50 μm. (D) At a higher magnification, endocytic vesicles can be seen on the control cells. Scale bar=5 μm.

Morphological differences between the EGF+bFGF-treated cells versus control cells were apparent under a light microscope (FIG. 10). The treated cells had a more compact cell body with extending neurite-like processes that appeared to connect with one another and form a cellular network (FIG. 10A). On the other hand, the control cells were not as elongated, and presented no visible neurite-like processes (FIG. 10B). To explore this morphological difference in depth, we examined the differences between the treated and control cell populations with a scanning electron microscope (SEM). Under the scanning electron microscope, both neural-like and glial phenotypes were observed in the culture containing the EGF+bFGF-treated cells (FIG. 11). The neural-like cells were easily distinguished by their rounded and raised cell bodies and very thin neurite-like processes (FIG. 11A, B). Glial-like cells appeared flatter and wider, with thicker processes that extend to neighboring cells (FIG. 11A). The untreated control cells looked very different and presented no morphological similarities to neural-like cells (FIG. 11C, D). In particular, the control cells did not demonstrate any extending processes, and seemed to coalesce as a sheet rather than form a network structure. These images suggest that treatment with EGF and bFGF effectively produces morphologically correct phenotypes of both glial and neuronal progenitor cells.

Figure 12:
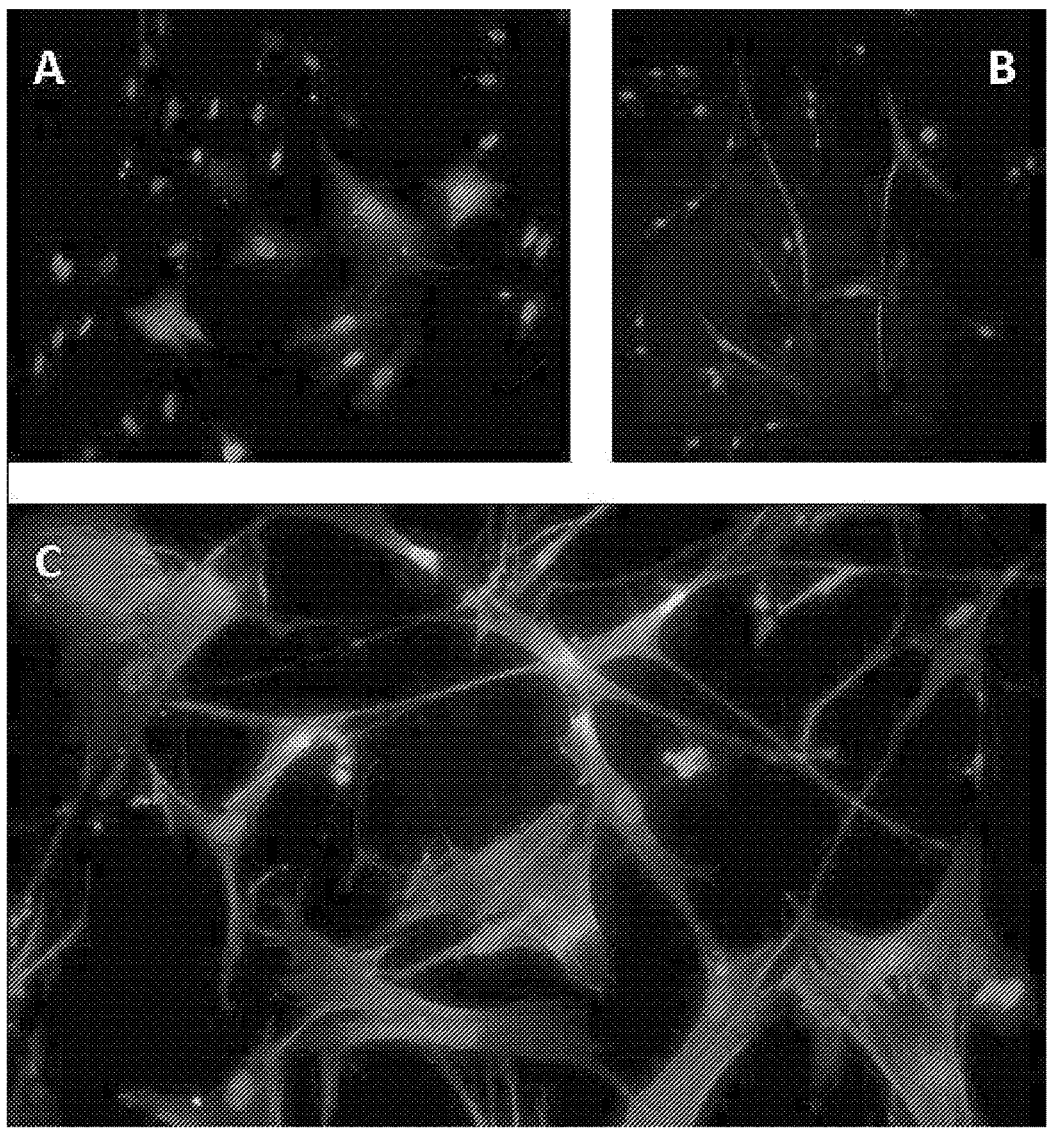
FIG. 12. Immunohistochemical staining of EGF+bFGF-treated and untreated PDLSCs. (A) Glial fibrillary acidic protein (GFAP)-labeled cells are observed in EGF+bFGF-treated PDLSC cultures. GFAP is green and DAPI, a nuclear marker, is shown in blue. (B) β-tubulin III (TUBB3)-labeled cells are observed in EGF+bFGF-treated PDLSC cultures. TUBB3 is red, and DAPI, a nuclear marker, is shown in blue. (C) Synaptophysin, a synaptic vesicle glycoprotein (shown in green/yellow), can be seen in EGF+bFGF-treated PDLSC cultures at the locations where one cell comes in contact with another cell. Alexa Flour 568 Phalloidin (staining the cytoskeleton) is in red, and DAPI, a nuclear marker, is in blue.

While the SEM images demonstrated positive morphological presentation of both glial and neuronal-like cells, to further verify the neural induction of the PDLSCs we employed immunohistochemical analyses. Immunohistochemical analysis of the EGF+bFGF-treated PDLSCs revealed positive staining for both neuron-specific β-tubulin III (TUBB3) and the astrocyte specific marker glial fibrillary acidic protein (GFAP) (FIG. 12). Corroborating the SEM micrographs, the cells that had a compact, raised, and rounded cytoplasm with neurite-like processes were indeed positive for TUBB3 (FIG. 12B), whereas the cells that had a flatter cytoplasm and broader processes stained positive for GFAP (FIG. 12A). The control cells, however, demonstrated no visible staining for either of these proteins (images not shown).

Synaptophysin, a synaptic vesicle glycoprotein commonly located pre-synaptically, was also present in the EGF+bFGF-treated group (FIG. 12C). No synaptophysin staining was observed in cells in the control group (images not shown). These findings further demonstrate that the neuro-induction protocol (e.g. treatment with EGF and bFGF) is effective at inducing PDLSCs to differentiate to a neural lineage, including both glial and neuronal populations.

Electrophysiology

Figure 13:
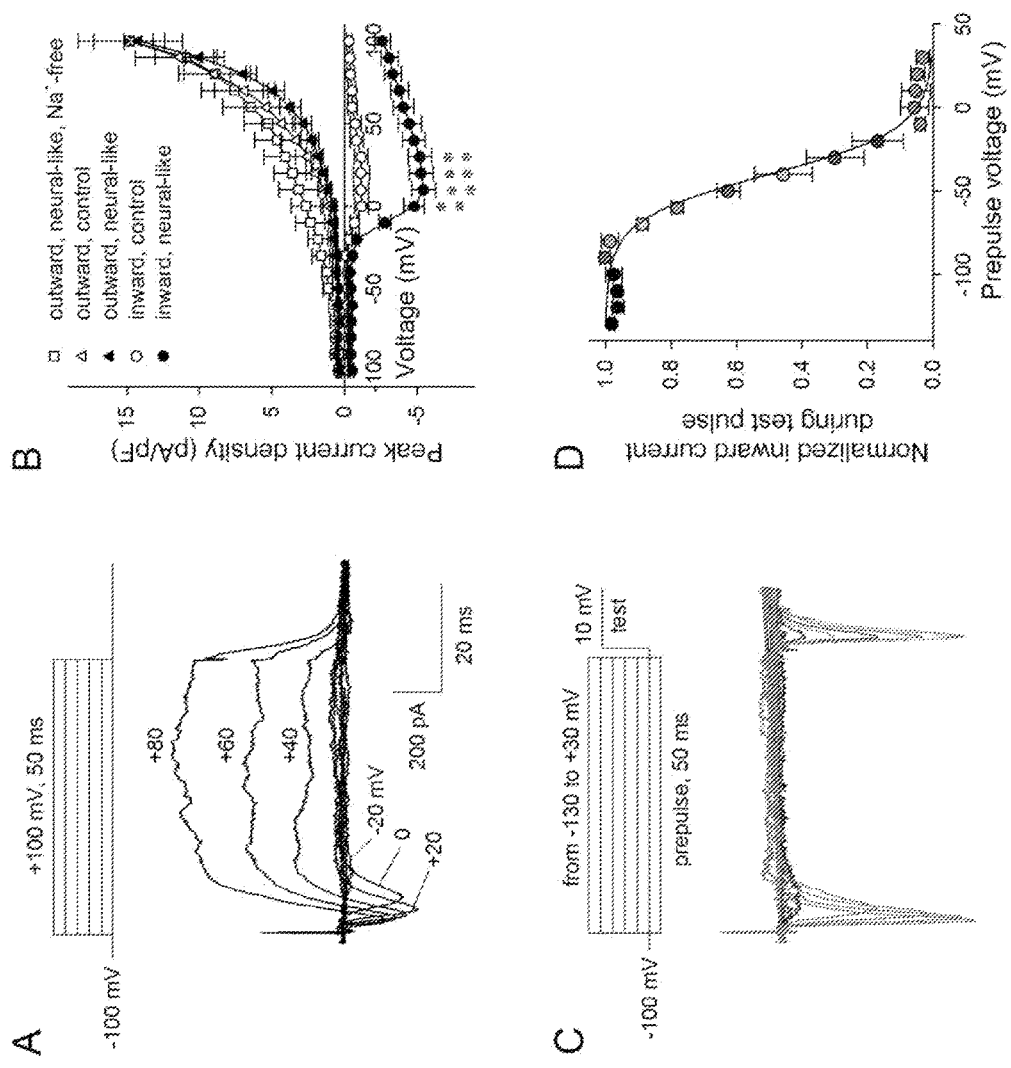
FIG. 13. Inward and outward currents of EGF+bFGF-treated and untreated PDLSCs. (A) Representative outward and inward currents from a differentiated, neural-like PDLSC following treatment with EGF+bFGF. Currents were elicited by voltage steps from a holding potential of −100 mV to various voltages, as illustrated above the current traces. Fast inactivating inward currents and slow but sustained outward currents are shown in 20 mV steps. (B) Peak outward and inward current densities, measured as current amplitude per unit cell capacitance (proportion to cell surface area), were plotted against testing pulse voltages. Error bars indicate standard error of the means. N=6 for both untreated, control and EGF+bFGF-treated (i.e. differentiated) cells. Significant differences (p<0.01, t-test) were found for the inward currents between control and neural-like PDLSC at the four voltages tested. (C) Voltage-dependent inactivation (a characteristic of voltage-gated sodium channels and T-type calcium channels) of the inward currents in a neural-like PDLSC was assayed with a traditional two-pulse protocol, where the current availability during the test pulse was used to evaluate the amount of inactivation during the first pulse or prepulse. Inward currents were induced similarly as in (A), but stepped briefly (1.5 ms) to −100 mV before tested again at +10 mV. Prepulse voltages are color-coded as in (D). (D) Voltage-dependent inactivation of the inward currents were normalized to the maximal and minimal currents in each cell before being averaged and fitted with the Boltzmann equation: $I/I_{max}=1/\{1+\exp[(V+40.0 \text{ mV})/13.55 \text{ mV}]\}$. N=4.

Following the positive immunohistochemical staining for synaptophysin we wanted to determine whether or not the growth factor-treated cells were beginning to have the electrophysiological properties of neural cells. Although preliminary current-clamping experiments on untreated, control PDLSC cells failed to elicit action potentials, voltage-clamp experiments demonstrated active ionic currents in EGF+bFGF-treated PDLSC. These cells contained both fast-inactivating inward and slow outward currents during voltage jumps to various voltages from a holding voltage of −100 mV (FIG. 13A). The fast-inactivating currents peaked around −10 mV, having kinetics and a range of activation similar to voltage-activated sodium currents. When the peak inward and outward currents were plotted against the testing voltage, they looked similar to the fast Na+ current and delayed-rectifier K+ currents in neurons (FIG. 13B). Interestingly, after treatment with EGF+bFGF, the neural-like PDLSC cells exhibited increased Na+-like current density, while the outward K+ current density stayed the same. To test if the increased inward currents were indeed Na+ currents, we replaced the Na+ in the external bath with N-methyl-D-glucamine chloride (NMDG), and found that no inward currents were observable, whereas the recorded outward currents slightly increased over the range where Na+-like currents were activated. These results were significantly different than those obtained from control cells (FIG. 13B). We also used a standard two-pulse protocol (FIG. 13C) to characterize the Na+ currents, and found voltage-dependent inactivation as is typical for voltage-dependent Na+ channels (FIG. 13D). As can be seen in FIG. 13C, the more channels that were activated during the prepulses, the fewer channels that remained available for opening during the second testing pulse at +10 mV. Fitting the inactivation curve with Boltzmann equation resulted in a half-inactivation voltage at −40 mV. As is commonly known, sodium channels are the basis for an action potential in neurons. These results indicate, therefore, that the inward current observed in PDLSCs treated with EGF+bFGF is a voltage-activated Na+ current, suggesting that the EGF+bFGF treatment induces neuronal differentiation of PDLSCs.

Taken together, the results of the experiments described in this example demonstrate that PDLSCs can be induced to differentiate into the neural lineage by treatment with EGF and bFGF. This neural induction protocol produced both glial and neuronal cell phenotypes. Thus, pre-treatment of PDLSCs with these growth factors can be employed prior to administration of the cells to a patient in need of neural cell regeneration. Pre-commitment of the PDLSCs to the neural lineage prior to administration to a patient can minimize the generation of unwanted cell types and facilitate neuronal repair.

Methods

RNA Extraction, cDNA Synthesis and qPCR

At the end of the treatment, cells used for gene expression analysis were collected and Trizol extraction was performed (Invitrogen, part of Life Technologies, Grand Island, N.Y.) per the manufacturer's instructions with the following modifications: centrifugation for phase separation and RNA precipitation was done at 14,000 rpm for 20 minutes. Centrifugation for the RNA wash was done at 7,500 rpm for 10 minutes. Total RNA yield was determined using the NanoDropND-1000 spectrophotometer (Thermo Scientific, Wilmington, Del.). Total RNA (1 µg) was converted to cDNA using the ABI High Capacity cDNA Reverse Transcription Kit (Applied Biosystems, part of Life Technologies, Grand Island, N.Y.) and the GeneAmp PCR System 9700 (Applied Biosystems, Grand Island, N.Y.). Quantitative PCR (qPCR) was performed using the Stratagene Mx3005P (Agilent Technologies, Santa Clara, Calif.). The samples were prepared using the Sybr Green PCR master mix (Applied Biosystems, part of Life Technologies, Grand Island, N.Y.), with 20 ng cDNA per reaction. The genes evaluated along with their primer sequences are in Table 1.

Immunohistochemistry

Following treatment and culture, cells used for immunohistochemistry were washed once with phosphate buffered saline (PBS). PBS was removed and cells were fixed with either 10% formalin (cell membrane markers) or 100% ice-cold methanol (intracellular markers) for 10 minutes. After removal of the fixative the cells were washed twice with PBS and remained in PBS at 4° C. until processed. Cell membrane marker samples were blocked for 1 hour in 5 mg/mL bovine serum albumin (BSA) in PBS. Intracellular marker samples were blocked for 1 hour in PBS+0.05% Tween 20+2% BSA+1% FBS. Immunostaining was carried out using the following primary antibodies and dilutions in 0.5 mg/mL BSA in PBS: synaptophysin—1:150 (Millipore, Billerica, Mass.), neuron-specific beta-tubulin III—1:100 (Abeam, Cambridge, Mass.), glial fibrillary acidic protein—1:1000 (Abcam, Cambridge, Mass.). Cells were left incubating in the primary antibodies overnight. The following day, the primary antibody was discarded and the cells were washed twice in PBS. The following secondary antibodies were applied diluted 1:200 in PBS: synaptophysin—Goat pAb to MsIgG (FITC), β-tubulin III—Bovine anti mouse IgG (R), GFAP—Goat pAb to RbIgG (FITC) (all secondary antibodies: Abcam, Cambridge, Mass.). The samples were shielded from light and incubated for 2 hours. For the synaptophysin staining, the secondary antibody was discarded following the 2 hour incubation and the samples were washed once with PBS. An Alexa Fluor 568 Phalloidin (Invitrogen, part of Life Technologies, Grand Island, N.Y.) was added to PBS at a 1:25 dilution and placed in the sample well. The sample was shielded from light and left to incubate for 30 minutes.

Following the 30 minute incubation, the Alexa Fluor was removed and the wells were washed once with PBS. For all samples, 2 drops of Vectashield hard set mounting media with DAPI (Fischer Scientific, Hampton, N.H.) was placed in each well. A glass coverslip was thoroughly washed, dried, and placed in each well. The samples were shielded from light and taken to image. Immunohistochemical images were acquired using a Nikon Digital Camera DS-Qi1MCmounted to a Nikon Eclipse Ti inverted fluorescent microscope. The NIS Elements software package was used for merging images and image analysis.

Scanning Electron Microscopy

Tissue culture coverslips (13 mm round) were coated for 5 minutes with 1% gelatin filtered through a 0.8 µm filter. After 5 minutes the gelatin was removed and the culture rounds were washed once with PBS. PDLSC were seeded unto the culture rounds at a density of 2500 cells/tissue culture round. All cells were plated using HGCCM. Cells were allowed to adhere to the tissue culture rounds overnight. Media was removed the following day and treatments were begun. The control cells were cultured in HGCCM for the duration of the experiment. EGF and bFGF were added to the EGF+bFGF treated group at a concentration of 50 ng/ml. Media was changed every 2 days for a total of 8 days of treatment. After completing the treatment, the media was removed and samples were fixed with Millonigs phosphate buffer+2.5% glutaraldehyde. Samples were kept at 4° C. until further processing. Once ready for processing the samples were rinsed 3 times for 5 minutes with the Millonigs phosphate buffer. Half strength Millonigs phosphate buffer was added to the samples with 1% OsO4 and left to incubate at room temperature for 1.5 hours. Following incubation the Millonigs and OsO4 were removed and the samples were once again rinsed 3 times for 5 minutes with Millonigs phosphate buffer. A dehydration series was performed with 50%, 70%, and 95% acetone where the acetone was added and incubated for 5 minutes, removed, and the same concentration was once again added and left for 10 minutes. Following the removal of the 95% acetone, 100% acetone was added to each sample and incubated for 10 minutes. The acetone was removed and addition of 100% acetone was repeated 3 more times for a total of 4 incubations with 100% acetone. The 100% acetone was decanted and critical point drying was performed using Hexamethyldisilazane (HMDS). A 2:1, 1:1, and 1:2 ratio of acetone to HMDS was added to the samples with wait times of 10 minutes in between removal and addition of HMDS. The 1:2 ratio of acetone:HMDS was removed and 100% HMDS was added to each sample. The samples were incubated for 5 minutes and the HMDS was removed. This was done one more time with 100% HMDS. The samples were removed from the HMDS and allowed to dry. The samples were then mounted onto 1 cm SEM sample stubs and sputter coated using a Hummer 6.2 sputter coater per the manufacturer's instructions. Samples were then imaged using a Jeol5600 LV Scanning Electron Microscope at 10 kV. Adobe Photoshop or Microsoft Publisher was used for image processing.

Electrophysiology 35 mm$^2$ dishes were plated with PDLSC at a density of 50 cells/dish. All cells were plated using HGCCM. Cells were allowed to adhere to the dishes overnight. Media was removed the following day and replaced with fresh HGCCM. Following an additional two days, the media was removed and the treatments were begun. EGF and bFGF were added to the EGF+bFGF treated group at a concentration of 50 ng/ml. Media was changed every 2 days for a total of 8 days of treatment. After completing the treatment, inward and outward currents were recorded in the whole-cell voltage-clamp configuration with an Axopatch 200A amplifier, Digidata 1322A interface, and pClamp9.0 software (Molecular Devices, Sunnyvale, Calif.). Data were sampled at 50 kHz and low-pass filtered at 5 kHz before off-line filtered at 2 kHz for final analysis. Borosilicate pipettes with 2-5 megaohm resistance were used when placed in the bath solution. The pipette solution contained (in mM): 130 K-gluconate, 10 KCl, 1 $MgCl_2$, 1 $CaCl_2$, 1 EGTA, and 10 HEPES, pH 7.2. The bath solution contained (in mM): 140 NaCl, 5 KCl, 2 $MgCl_2$, 2 $CaCl_2$, 10 glucose, and 10 HEPES, pH 7.4. For sodium-free experiments the K-gluconate and KCl in the pipette solution were replaced by 140 mM CsCl, and the NaCl in the bath solution was replaced by 140 mM N-methyl-D-glucamine chloride. Leaks and capacitive transients were online subtracted using the p/−4 or p/−5 leak subtraction routine.

Example 4. Induction of Adult Human Periodontal Ligament-Derived Stem Cells to Retinal Fate As described in Example 2, adult human periodontal ligament-derived stem cells (PDLSCs) are pluripotent and have the capacity to differentiate into multiple lineages. To investigate whether PDLSCs could be directed to attain a retinal fate, PDLSCs were treated with Noggin (antagonist of BMP signaling), Dkk-1 (antagonist of Wnt/β-catenin signaling) and insulin-like growth factor-1 (IGF1) to mimic the signaling systems active during mammalian retinogenesis.

Primary human periodontal ligament (PDL) cultures were established from healthy subjects under the age of 35 with informed consent. Within six hours from tooth extraction, PDL tissue was scrapped mechanically from the root surface, finely chopped and digested with 0.1% collagenase I and III (Worthington, Lakewood, N.J.) in culture medium added with 0.5% fetal bovine serum (FBS, Invitrogen, Eugene, Oreg.) and antibiotics for 4 to 6 hours with agitation at 37° C. (Huang et al., 2009). After passing through cell strainer (40 µm pore size, BD, Franklin Lakes, N.J.), the single cells were cultured in DMEM/F12 medium (Invitrogen) supplemented with 10% FBS, 100 U/ml penicillin sulfate, 100 µg/ml streptomycin and 1% antimycotics.

Figure 14:
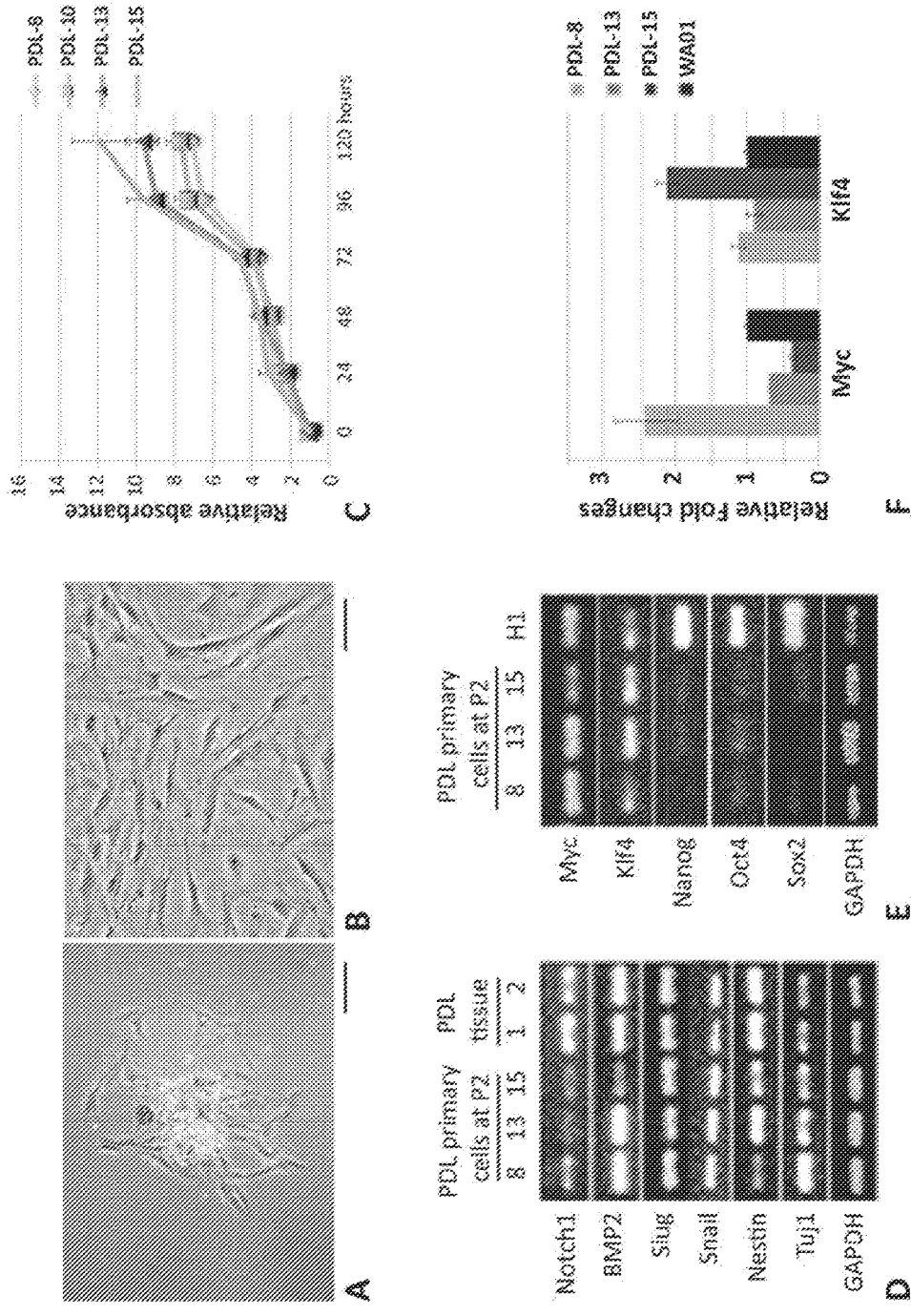
FIG. 14. Primary human PDLSC culture and characterization. (A) A representative colony of primary cells in culture for 4 days. (B) Stellate and spindle-shaped cells at day 14 of culture. (C) Growth curves of PDL-8, 10, 13 and 15 cells at passage 2. Each point represents mean±standard deviation from triplicate experiments. (D) RT-PCR analysis showing the expression of neural crest genes (Notch1, BMP2, Slug, Snail, Nestin and Tuj1) in primary PDL-8, 13 and 15 cells at passage 2. The expression levels were compared to two freshly dissected PDL tissues. (E) PDL cells expressed ES pluripotency genes, c-Myc and Klf4, at comparable levels as human ES H1 cells, but Nanog, Oct4 and Sox2 had negligible expression. The relative fold changes of c-Myc and Klf4 among primary PDL and H1 cells are shown in (F).

Twenty five primary human PDL cultures from adult Chinese subjects below age of 35 were established. From our cell culture record, all teeth samples showed similar efficiency of PDL cell isolation, irrespective of variation of age and sex. Normally, within 5 days of initial seeding, P1 PDLSCs displayed clonogenic growth of 6 to 8 cells. The adherent cells continued to proliferate and the colony size increased substantially in the first 3 to 4 days. Cells in the center of colony were more densely packed than those in periphery (FIG. 14A). We frequently observed more migratory cells in the peripheral region (data not shown). Most cells were spindle to slender in shape at early culture time. After 14 days in culture, the cells displayed dendritic morphology with distinct cell nuclei and more intercellular connection at ends of dendritic processes (FIG. 14B). Some cells exhibited a more flattened morphology, whereas other cells had more compact and crescent shapes.

Figure 15:
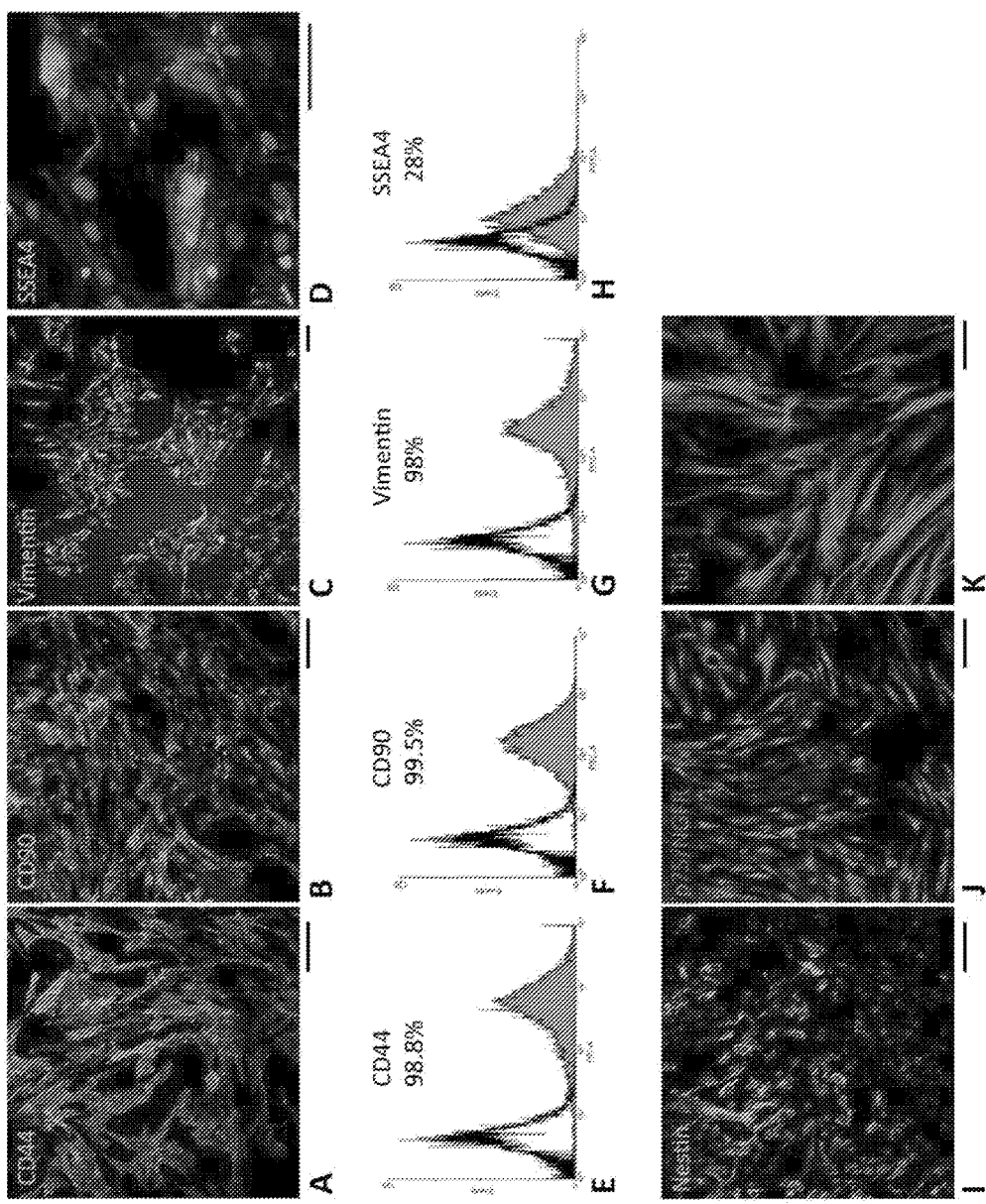
FIG. 15. (A to D, I to K) Representative confocal immunofluorescence images showing the vast expression of MSC markers (A, CD44; B, CD90 and C, vimentin), ES cell marker (D, SSEA-4) and neural crest markers (I, Nestin; J, p75/NGFR and K, Tuj1) in PDL-8 at passage 2. Nuclei were counterstained with DAPI (blue). Scale bars, 50 μm. (E to H) Flow cytometric histograms showing event profile of (E) CD44, (F) CD90, (G) vimentin and (H) SSEA4. Open histograms denote the isotype control.

Four primary PDLSCs from patients of younger age range were randomly selected for further study (PDL-8: female/21 years old; PDL-10: female/13; PDL-13: male/16 and PDL-15: female/33). All cells at passage 2 had similar growth rate (FIG. 14C). The mean cell doubling time was 25-30 hours at the exponential growth phase. The cells stably expressed neural crest markers (Notch1, BMP2, Slug, Snail, Nestin and Tuj1) as shown by real-time PCR analysis (FIG. 14D). The expression was similar as the PDL tissues freshly isolated from the root surface. This expression profile was consistent in all 25 primary PDLSCs, irrespective to age and sex variation. Representative staining of PDL-8 cells with antibodies recognizing Nestin, p75/NGFR, and Tuj1 is shown in FIG. 15I-K. In addition to the Nestin staining in >90% of the cells, the majority (>95%) of cells were immunopositive for p75/NGFR and Tuj1 (FIG. 15I-K). This was supported by flow cytometry analysis (data not shown). The cells also expressed a set of mesenchymal stem cell (MSC) markers (CD44, CD90 and vimentin), as shown by immunofluorescence (FIGS. 15A-C) and flow cytometry (FIGS. 15E-G). On the other hand, PDLSCs exhibited variable expression of pluripotency genes. Although the cells had comparable expression levels of c-Myc and Klf4 to those of human ES H1 cells, Oct4, Sox2 and Nanog were barely expressed (FIGS. 14E-F). SSEA-4 was only expressed in a subset of PDLSCs (FIG. 15D) and flow cytometry showed 28% were SSEA-4 positive (FIG. 15H).

Neural Retinal Fate Commitment from Human PDLSCs

Figure 16:
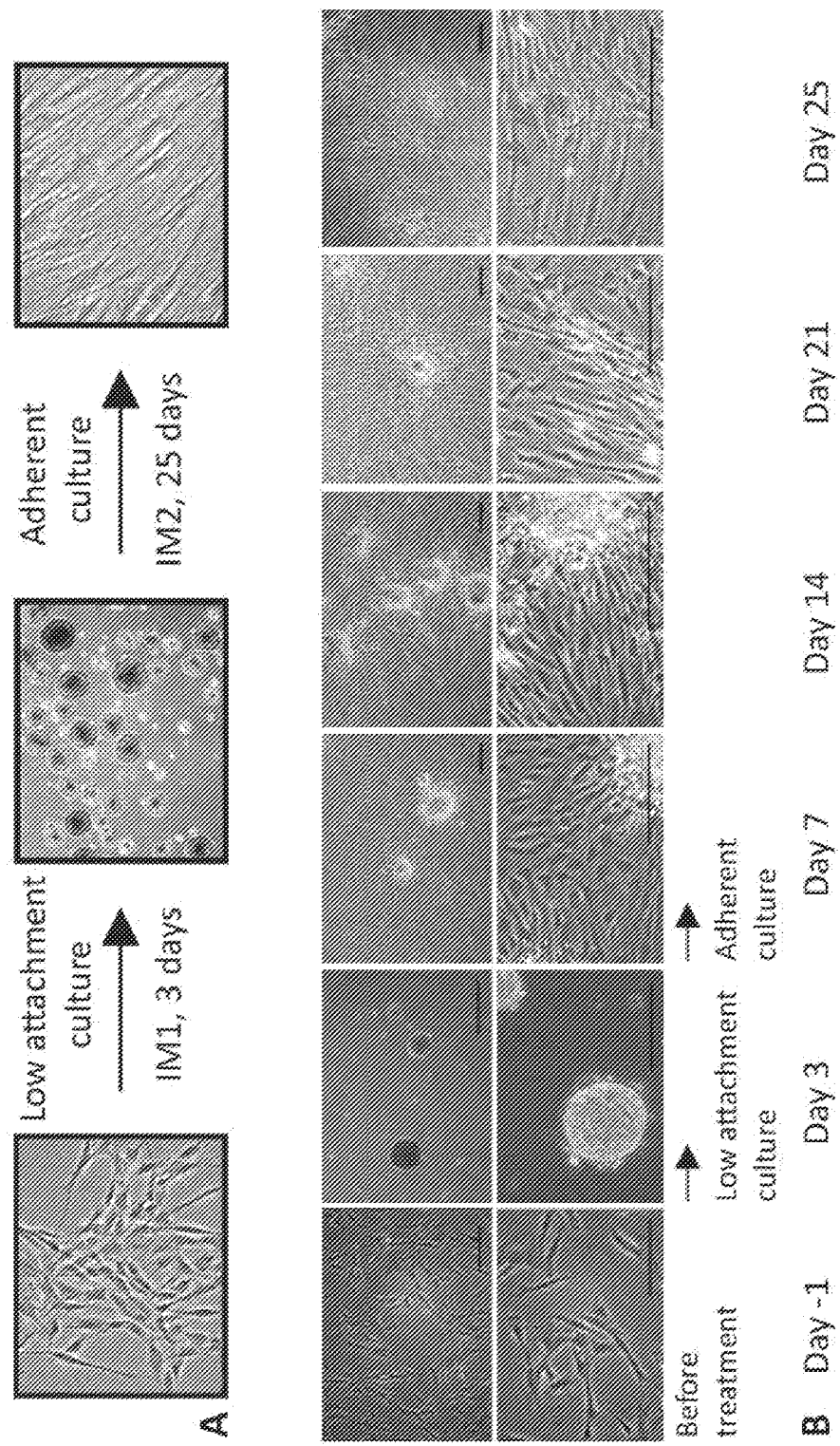
FIG. 16. Retinal fate induction of primary PDL cells. (A) A schematic illustration of retinal fate induction of PDL cells towards the formation of neurospheres by floating culture and neuron-like cells by adherent culture. (B) Cell morphology changes of PDL cells at time intervals of induction. Scale bars, 200 μm.

To test the capacity of PDLSCs to differentiate towards a retinal progenitor fate, a two-step differentiation protocol was employed involving initial neurosphere formation followed by propagation as adherent cultures (FIG. 16A-B). Specifically, PDLSCs at passage 3 were recruited for a 2-step retinal fate induction procedure. Step 1 was to obtain neurospheres by culturing cells with induction medium 1 (IM1), which was DMEM/F12 supplemented with B27 (Invitrogen), 1 ng/ml mouse Noggin (R&D Systems), 1 ng/ml human recombinant Dkk-1 (R&D Systems) and 5 ng/ml human recombinant IGF-1 (R&D Systems), under an attachment-free condition for 3 days. Step 2 was to plate neurospheres on matrigel-coated surface in induction medium 2 (IM2) (same composition as IM1, except for the addition of N2 (Invitrogen) and Noggin and Dkk-1 were added to a final concentration of 10 ng/ml each). Fresh medium was replenished every 3 days and culture was maintained for up to 25 days.

Figure 17:
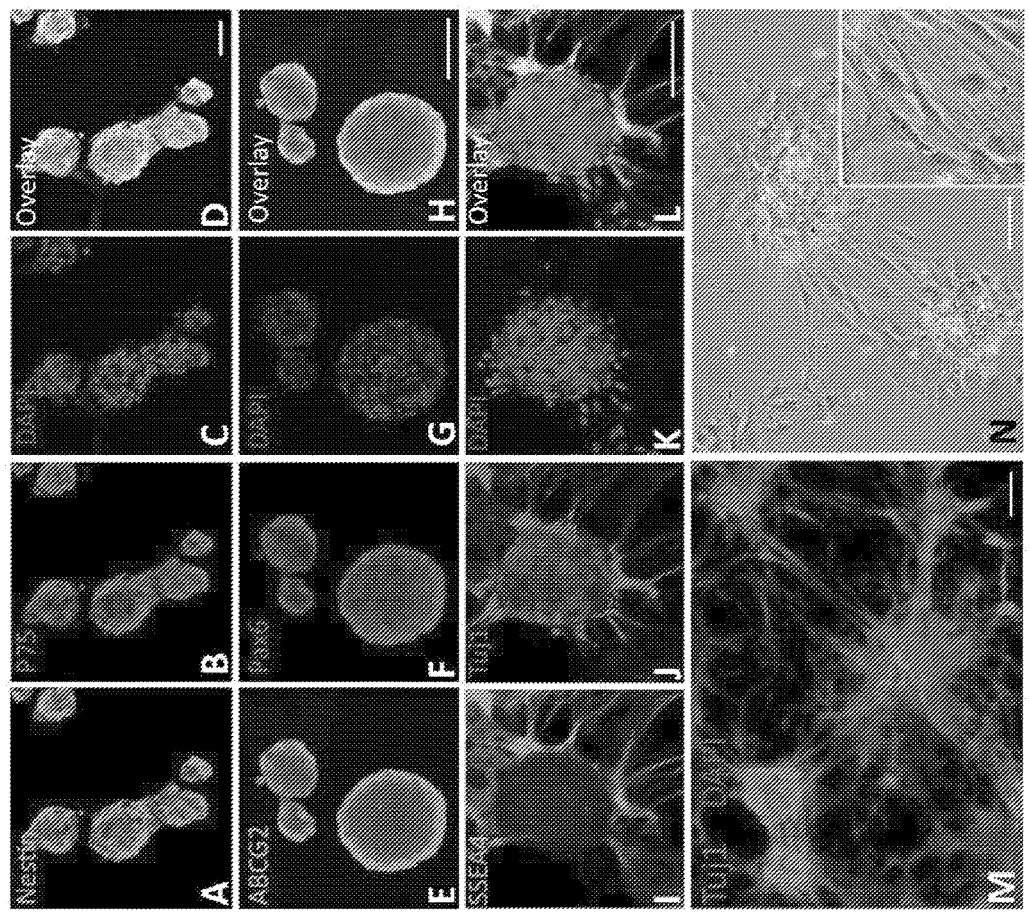
FIG. 17. Characterization of PDLSC-derived neurospheres. The neurospheres at day 3 of low attachment culture were collected and assayed for expression of (A) Nestin, (B) p75/NGFR, (E) ABCG2, (F) Pax6, (I) SSEA4 and (J) Tuj1. (C, G, K) All nuclei were counterstained with DAPI and (D, H, L) were merged images of respective staining. (M) Low magnification picture showing neurite-like processes extending from neurospheres. (N) Phase contrast micrograph of neurospheres attached on matrigel-coated surface at day 3 of culture. The insert shows neurites between spheres. Scale bars, 50 μm.

Human PDLSCs were sensitive to this free-floating culture system and generated neurospheres rapidly and efficiently. The neurospheres expanded for 3 days were immunopositive for a variety of neural stem and precursor markers including Nestin, p75, ABCG2 and Pax6 (FIG. 17A-H). The vast majority of the Nestin expressing cells were p75 reactive, and ABCG2 was often coexpressed with Pax6. In addition, greater than 95% of the cells within neurospheres were labeled with Tuj1, while cells expressing SSEA4 were found predominantly in the outer portions of neurospheres (FIG. 17I-L). Interestingly, some cells around neurospheres showed Tuj1 positive exhibiting long neurite like processes and extended to adjacent neurospheres forming networks (FIG. 17M-N).

Figure 18:
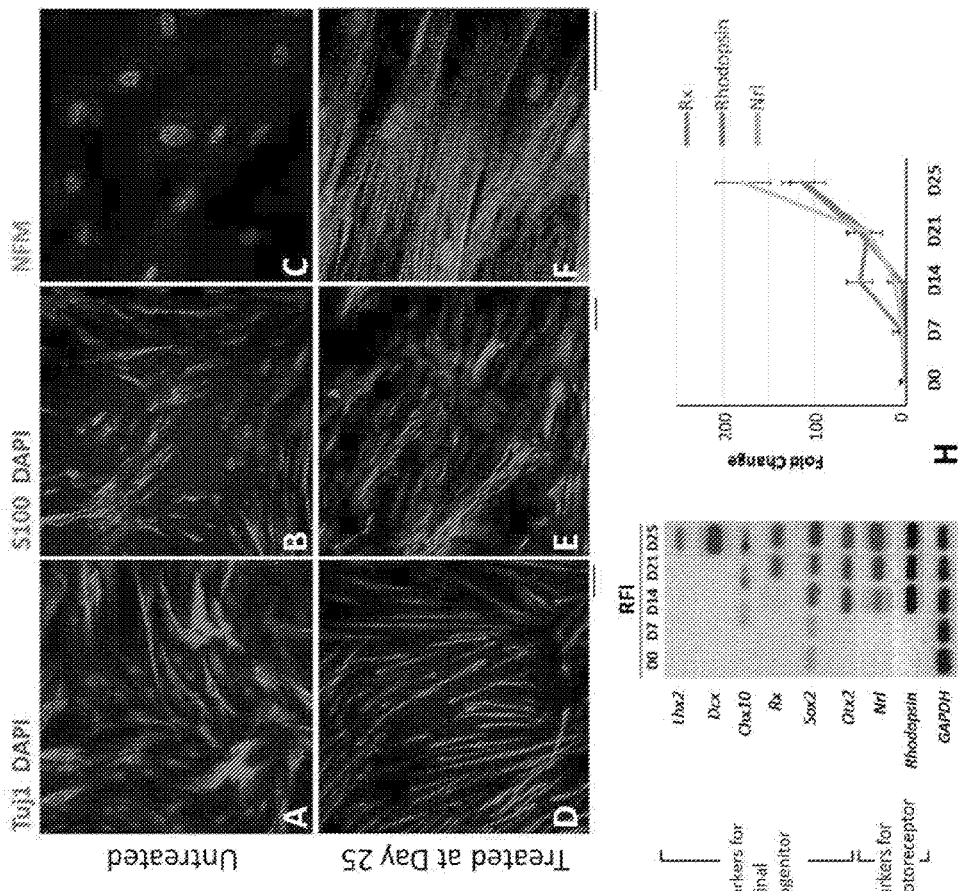
FIG. 18. Retinal lineage commitment of human PDLSC. (A-F) Immunostaining of neuronal markers (Tuj1, S100 and NFM) at day 25 of treatment (D-F), when compared to untreated control (A-C). Scale bars: 50 μm. (G and H) RT-PCR and qPCR analyses showing an up-regulation of genes identifying retinal progenitors (Lhx2, Dcx, Chx10, Rx, Sox2, Otx2) and photoreceptors (Nrl and rhodopsin) at various time intervals during treatment.

When the neurospheres were plated on Matrigel-coated surface in IM2 condition (with 10 ng/ml Noggin and Dkk-1, and N2 supplement), they attached and formed rosette-like outgrowth (FIG. 16B). Majority of cells exhibited extended projections and neurite-like morphology after treatment for 25 days (FIG. 16B). Neuronal lineage differentiation was evidenced by immunoreactivity for a variety of neuronal markers (including Tuj1, S100, p75 and neurofilament M) (FIG. 18A-F). At intervals during IM2 treatment, the cells were harvested and RT-PCR analysis revealed that there was gradual up-regulation of multiple genes associated with eye field specification (Lhx2, Dcx, Chx10, Rx, Sox2, and Otx2) (FIG. 18G). Up to 110-fold increase in Rx level was detected at day 25 of IM2 treatment, when compared to untreated control cells by qPCR (FIG. 18H). Minor alterations in the expression levels of different neural crest related genes (Tuj1, Nestin, Snail and Slug) were found during the induction course (data not shown).

Pax6 Activation by Retinal Fate Induction

Figure 19:
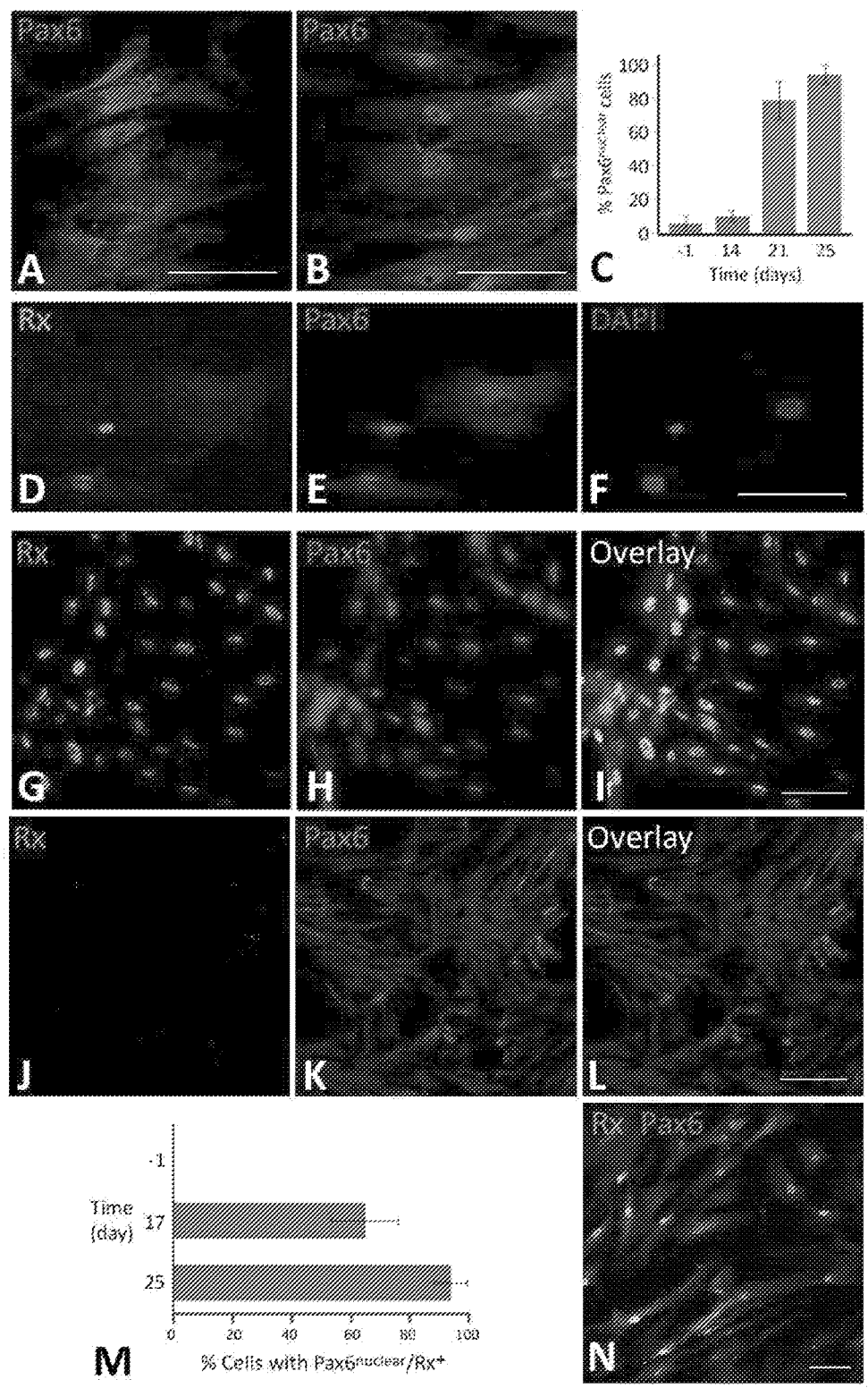
FIG. 19. PDLSCs express Pax6 and Rx under retinal fate induction. Confocal immunofluorescence pictures showing Pax6 localization in (A) untreated cells and (B) cells treated for 25 days. Significant nuclear translocation of Pax6 was detected after induction. (C) Percentage of cells with nuclear Pax6 increased during treatment. The data represented mean±SD from three independent experiments. (D-F) Rx was induced in cells with Pax6 nuclear expression. Nuclei were counterstained with DAPI. (G-I) Expression of Pax6 nuclear Rx+ cells at 25 days of induction, when compared to (J-K) control cells at day −1. (M) Percentage of Pax6 nuclear Rx+ cells increased during treatment. (N) A representative picture of Pax6 nuclear Rx+ cells at day 17 of experiment. All quantitative data in (C) and (M) represented mean±SD from three independent experiments. Scale bars, 50 μm.

Untreated PDLSCs had a diffuse cytoplasmic expression of Pax6, as shown by immunofluorescence in FIG. 19A. After 25 days of IM2 incubation, we observed a clear nuclear translocation of Pax6 (FIG. 19B-C). Interestingly, these cells were associated with Rx induction. Rx was exclusively expressed in $Pax6^{nuclear}$ cells and vice versa (FIG. 19D-I). By cell counting analysis of >500 cells, we detected that retinal fate induction (RFI) resulted in 94.6±4.7% cells becoming $Pax6^{nuclear}+$, when compared to 0% cells without RFI. Such expression phenotype indicated high efficient conversion of PDL cells to retinal progenitors.

In addition, the active state of the induced hPDLSCs-derived retinal progenitor-like cells was evaluated by cell-cycle regulators Cyclin A and p21 expression. Compared with untreated PDLSCs, day 25 differentiated PDLSCs showed stronger staining for Cyclin A. Consistently, Western blotting results demonstrated high protein content of Cyclin A with concomitant downregulation of p21 expression and constant expression of PCNA after the 10×NDI treatment. These findings indicate the PDLSCs-derived retinal progenitor-like cells are proliferative and mitotically active.

Acquisition of Photoreceptor Phenotypes

Figure 20:
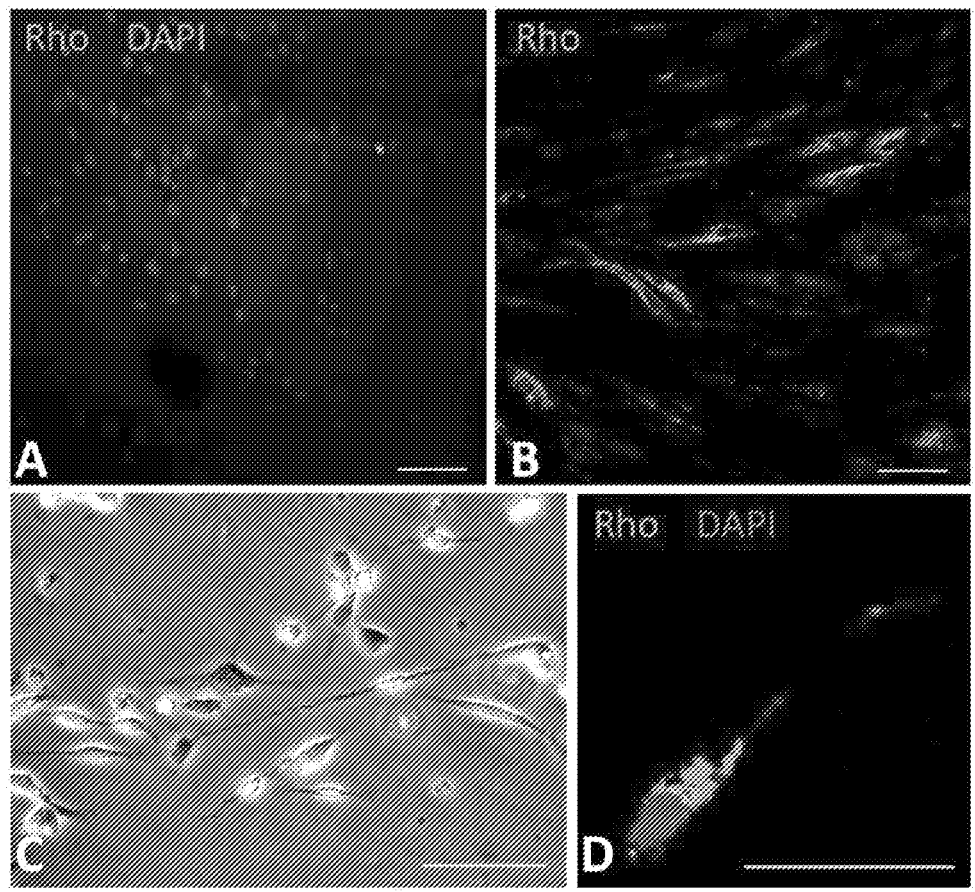
FIG. 20. Photoreceptor fate of PDLSCs under induction. Compared to control cells (A), treated cells (B) at day 25 exhibited rhodopsin expression. (C-D) Cells under prolonged treatment for 45 days displayed dendritic morphology (C) and rhodopsin (Rho) expression in the cell body as well as along the neurite process (D). Nuclei in (A) and (D) were counterstained with DAPI. Scale bars, 50 μm. (E) Western blot analysis showing elevated rhodopsin kinase at day 25 of retinal fate induction. Expression of proliferating cell nuclear antigen had negligible change. β-Actin served as the housekeeping control.
Figure 20:
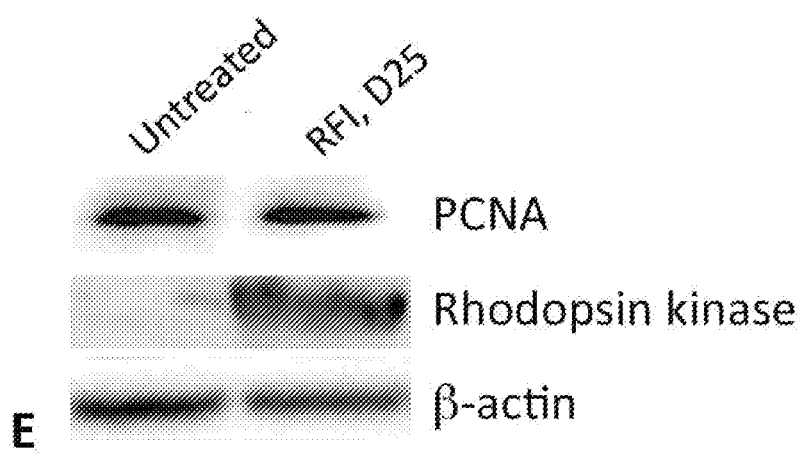

To determine if PDLSC-derived retinal progenitors could obtain photoreceptor phenotype under RFI condition, we examined the expression of photoreceptor markers. Our RT-PCR result revealed that Nrl and rhodopsin gene expression was detected as early as day 14 of IM2 treatment (FIG. 18G). Both genes were up-regulated by 180 and 110 folds, respectively (FIG. 18H). At day 25, 5.1±0.5% cells expressed rhodopsin (FIG. 20B), the rod-specific marker. Rhodopsin kinase, an enzyme involved in rhodopsin biosynthesis in rod photoreceptors was obviously up-regulated in IM2 treated cells (FIG. 20E). When IM2 treatment was prolonged to day 45, PDL cells stopped dividing and developed a small, round cell body and single, thin processes, morphological characteristics of photoreceptors (FIG. 20C).

Electrophysiological Properties of the PDLSC-Derived Retinal Neuron-Like Cells

Figure 21:
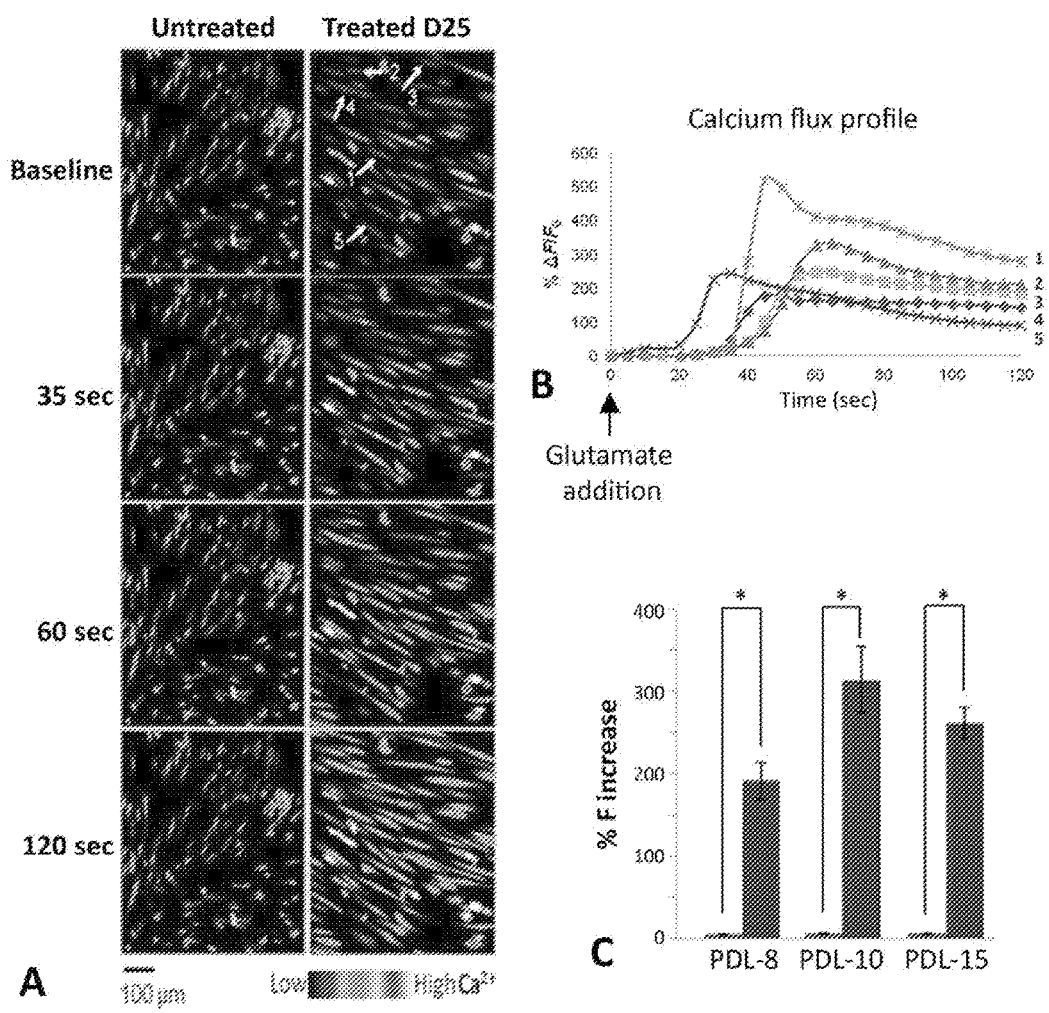
FIG. 21. Glutamate evokes calcium influx in PDLSCs under retinal fate induction. (A) Representative pseudo-color images of Fluo-4 AM fluorescence in untreated and treated PDLSCs (day 25) after 1 mM glutamate insult for 35, 60 and 120 sec. The color code denotes the calcium level. Scale bar, 100 µm. (B) Calcium flux profiles of 5 randomly selected cells (indicated in A upper right image). The fluorescence intensity change was represented as % ΔF/F0. The detection was carried out until 120 sec of glutamate stimulation. (C) Peak calcium responses in treated cells (PDL-8, 10 and 15) at day 25 was compared to baseline levels. All data are mean±SD, determined from 50 cells in 3 separate experiments. * $P<0.001$ (paired Student's t-test).

To identify the functional membrane properties of the PDLSC-derived retinal neurons, the intracellular $Ca^{2+}$ level in response to glutamate was examined via fluo-4 imaging. Day 25 differentiated PDLSCs showed spontaneous responses to glutamate stimulation producing rapid and robust increase of fluo-4 fluorescence intensity (FIG. 21A). Approximately 92% of the differentiated PDLSCs responded to glutamate (184 responsive cells in 200 cells from 3 separate experiments). Most of the increases occurred during the first 40 seconds, peaked in 60-80 s after scan onset and then decayed slowly, although the response kinetics in time course and stimulus intensity varied between cells (FIG. 21B). Electrophysiological recordings showed that 191±108% (mean±SD) of peak glutamate responses were detected in Day 25 differentiated PDLSCs, which was significant greater than that in untreated PDLSCs (P<0.001; FIG. 21C). These strong (an average of 191%ΔF/F0) and spontaneous glutamate-evoked fluorescence intensity increases with $Ca^{2+}$ influx in PDLSC-derived retinal neuron-like cells is consistent with previous observations in retinal progenitors and photoreceptor precursors (Tucker et al., 2011), suggesting the differentiated cells may obtain excitable membrane properties corresponding to developing retinal neurons.

The results of the experiments in this example show that pluripotent adult PDLSCs can be directed to adopt a retinal fate with competence of photoreceptor differentiation by treatment with Noggin, Dkk-1, and IGF-1. Our findings suggest that adult PDLSCs are a novel and crucial autologous cell source for retinal lineage differentiation and future design of retinal repair and regeneration for the treatment of retinal degenerative diseases.

Methods

Cell Proliferation Assay

Primary cells at passage 2 were seeded at a density of $5×10^3$ cells/well in a 96-well plate. Cell proliferation was assessed by MTT method at different time intervals. MTT (0.5 mg/ml, Sigma, St Louis, Mo.) was applied to cells in culture for 3 hours, and isopropanol was added to dissolve formazan crystals. The solution absorbance was determined by spectrophotometery with excitation wavelength at 590 nm (PowerWave microplate reader, BioTek Instru Inc., Winooski, Vt.). Results from triplicate experiments were represented as mean±standard deviation (SD).

Immunocytochemistry

Cells were fixed with freshly prepared 2% neutral buffered paraformaldehyde and permeabilized with 0.15% saponin (Sigma). After blocking, the samples were incubated with primary antibodies (Table 2) and subsequently with either Alexa 488 or Rhodamine Red-X-conjugated secondary antibodies (Jackson ImmunoRes Lab), and all nuclei were counterstained with DAPI (4',6-diamidino-2-phenylindole, Invitrogen). Result was visualized using confocal laser scanning microscopy (SP5, Leica). A minimum of 10 fields viewed at 20× magnification (objective) were taken for cell quantification. The percentage of labeled cells in triplicate experiments was expressed as mean±SD. Result was compared between control and treated samples and analyzed by paired Student's t-test and P<0.05 was considered as statistically significant.

TABLE 2

Primary antibody list

| Antibody | Type | Source | Dilution |
|---|---|---|---|
| CD44 | Mouse monoclonal | Pharmingen | 1:200 |
| CD90 | Mouse monoclonal | Pharmingen | 1:200 |
| Neurofilament-M | Mouse monoclonal | DAKO | 1:200 |
| Nestin | Mouse monoclonal | Chemicon | 1:200 |
| p75/NGFR | Rabbit polyclonal | Promega | 1:200 |
| Pax6 | Rabbit polyclonal | Covance | 1:150 |
| PCNA | Mouse monoclonal | Zymed | 1:500 |
| Rhodopsin | Mouse monoclonal | Thermo | 1:100 |
| Rhodopsin Kinase | Mouse monoclonal | Thermo | 1:500 |
| Rx | Mouse monoclonal | Santa Cruz | 1:150 |
| S100 | Rabbit polyclonal | DAKO | 1:200 |
| SSEA4 | Mouse monoclonal | Stemgent | 1:200 |
| βIII tubulin | Rabbit monoclonal | Covance | 1:200 |
| Vimentin | Mouse monoclonal | DAKO | 1:200 |

Flow Cytometry

Trypsinized cells were washed and fixed with 2% paraformaldehyde in DMEM/F12 medium containing 2% bovine serum albumin for 20 min. After washes, they were incubated with primary antibodies (Table 2) or isotype control for overnight at 4° C., followed by either donkey-anti-mouse or donkey-anti-rabbit Alexa 488 secondary antibodies for another 2 hours at ambient temperature. Single cell suspension after passing through a cell strainer (40 μm pore diameter) was analyzed by before flow cytometry (LSR Fortessa flow cytometer, BD Biosciences) and a minimum of 10,000 events was recorded for each sample for data analysis using FACS Diva software.

Gene Expression Analysis

Cells were collected in RLT buffer freshly added with 1% β-mercaptoethanol and total RNA was extracted by RNeasy kit (Qiagen) according to manufacturer's protocol. Reverse transcription of 1 μg total RNA was performed with Superscript III RT-PCR kit (Invitrogen) using random hexanucleotide primers. Gene expression was assayed by PCR using Master Mix (Invitrogen) and specific primers (Table 3) and PCR products were resolved by agarose gel electrophoresis. Alternatively, quantitative real-time PCR (qPCR) was performed with Sybr Green Supermix (Applied Biosystems) in ABI PRISM 7900HT Sequence Detection System (Applied Biosystems). Experiments were run in triplicate. Relative gene expression of each sample was normalized by the mean CT value to housekeeping GAPDH ($CT_{GAPDH}$) and expressed as mean±SD.

TABLE 3

Gene expression primers

| Gene | GeneBank Accession No. | Sequences (5'-3') | Amplicon size (bp) |
|---|---|---|---|
| Chx10 | NM_182894.2 | F: ATTCAACGAAGCCCAC TACCCA (SEQ ID NO: 13) R: ATCCTTGGCTGACTTG AGGATG (SEQ ID NO: 14) | 229 |
| cMyc | NM_002467.4 | F: CTACCCTCTCAACGAC AGCA (SEQ ID NO: 15) R: GTTCCTCCTCAGAGTC GCTG (SEQ ID NO: 16) | 179 |
| DCX | NM_000555.3 | F: GACAGCCCACTCTTTT GAGC (SEQ ID NO: 17) R: TGGGTTTCCCTTCATG ACTC (SEQ ID NO: 18) | 229 |
| GAPDH | NM_002046.3 | F: GAACATCATCCCTGCA TCCA (SEQ ID NO: 19) R: CCAGTGAGCTTCCCGT TCA (SEQ ID NO: 20) | 226 |
| Klf4 | NM_004235.4 | F: CAGGTGCCCCAGCTGC TTCG (SEQ ID NO: 21) R: CCCGCCAGCGGTTATT CGGG (SEQ ID NO: 22) | 188 |
| Lhx2 | NM_004789.3 | F: CAAGATCTCGGACCGC TACT (SEQ ID NO: 23) R: CCGTGGTCAGCATCTT GTTA (SEQ ID NO: 24) | 284 |

TABLE 3-continued

Gene expression primers

| Gene | GeneBank Accession No. | Sequences (5'-3') | Amplicon size (bp) |
|---|---|---|---|
| Nanog | NM_002865.2 | F: CTGCAGAGAAGAGTGT CGCA (SEQ ID NO: 25) R: GGTCTTCACCTGTTTG TAGCTG (SEQ ID NO: 26) | 188 |
| Nestin | NM_006617.1 | F: CAGGAGAAACAGGGCC TACAGA (SEQ ID NO: 27) R: TCCAGCTTGGGGTCCT GAA (SEQ ID NO: 28) | 191 |
| Notch1 | NM_017617.2 | F: CCTGAGGGCTTCAAAG TGTC (SEQ ID NO: 29) R: CGGAACTTCTTGGTCT CCAG (SEQ ID NO: 30) | 164 |
| Nrl | NM_006177.2 | F: GGCTCCACACCTTACA GCTC (SEQ ID NO: 31) R: CTGGGCTCCCTGGGTA GTAG (SEQ ID NO: 32) | 219 |
| Oct4 | NM_002701.4 | F: CTTCAGGAGATATGCA AAGCAG (SEQ ID NO: 33) R: GCTGATCTGCTGCAGT GTG (SEQ ID NO: 34) | 135 |
| Otx2 | NM_021728.2 | F: GCAGAGGTCCTATCCC ATGA (SEQ ID NO: 35) R: CTGGGTGGAAAGAGAA GCTG (SEQ ID NO: 36) | 211 |
| Rhodopsin | NM_000539.1 | F: CGGAGGTCAACAACGA GTC (SEQ ID NO: 37) R: TCTCTGCCTTCTGTGT GGTG (SEQ ID NO: 38) | 156 |
| Snail | NM_005985.3 | F: GACCCCAATCGGAAGC CTAACTA (SEQ ID NO: 39) R: AGCCTTTCCCACTGTC CTCATCT (SEQ ID NO: 40) | 164 |
| Slug | NM_003068.4 | F: TTCGGACCCACACAT TACCT (SEQ ID NO: 41) R: GCAGTGAGGGCAAGAA AAAG (SEQ ID NO: 42) | 122 |
| Sox2 | NM_003106.3 | F: CCCCCCTGTGGTTAC CTCTT (SEQ ID NO: 43) R: GCTGGGACATGTGAAG TCTGC (SEQ ID NO: 44) | 137 |

TABLE 3-continued

Gene expression primers

| Gene | GeneBank Accession No. | Sequences (5'-3') | Amplicon size (bp) |
|---|---|---|---|
| βIII tubulin | NM_006086.3 | F: ACCTCAACCACCTGG TATCG (SEQ ID NO: 45) R: TTCTTGGCATCGAACA TCTG (SEQ ID NO: 46) | 223 |

Western Blotting

Cells were collected in lysis buffer, containing 50 mM Tris-HCl, 150 mM sodium chloride, 1% Nonidet P-40, 0.25% sodium deoxycholate, protease inhibitor cocktail (Complete™, Roche) and 1 mM phenylmethyl sulfonylfluoride. The clear soluble lysate was heat-denatured with 2% sodium dodecylsulfate (SDS, weight/volume). The samples were resolved with SDS-PAGE (polyacrylamide gel electrophoresis), blotted and immunolabeled with primary antibodies (Table 2) followed by appropriate horseradish peroxidase-conjugated Ig secondary antibodies (Jackson ImmunoRes Lab). Signal was detected by enhanced chemiluminescence (ECL, GE Healthcare, Pittsburgh, Pa.).

Calcium Imaging Assay in Response to Glutamate Stimulation

Intracellular calcium transient was evaluated using fluo-4-acetoxymethyl (Fluo-4AM) ester (Invitrogen). Cells were incubated in balanced salt solution containing 5 μM Fluo-4AM, 0.1% pluronic F-127 (Sigma) for 30 min at room temperature. Fluorescence image was captured using Olympus Fluoview FV1000 laser scanning confocal system (Olympus, Melville, N.Y.), with excitation wavelength at 495 nm and emitted wavelength at 515 nm, at every 5 sec for a total of 2 minutes. Stimulation by glutamate (1 mM, Sigma) was performed. Data was analyzed using Olympus FV10-ASW version 1.7. The change of fluorescence (F) (%ΔF/$F_{baseline}$) of each cells were calculated as: $(F_{treated} - F_{baseline})/F_{baseline} \times 100\%$. A minimum of 10 cells of each sample at specific time interval was recorded for fluorescence calculation using FACS Diva software.

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

REFERENCES

Bronner M E. Formation and migration of neural crest cells in the vertebrate embryo. Histochem Cell Biol. 2012 August; 138(2):179-86.

Cardozo A J, Gómez DE, Argibay P F. Neurogenic differentiation of human adipose-derived stem cells: Relevance of different signaling molecules, transcription factors, and key marker genes. Gene. 2012 Sep. 18. pii: S0378-1119(12)01119-5.

Cheng Z, Zheng Q, Wang W, Guo X, Wu Y, Zheng J. Targeted induction of differentiation of human bone mesenchymal stem cells into neuron-like cells. J Huazhong UnivSci Technolog Med Sci. 2009 June; 29(3):296-9.

Conrad S, Renninger M, Hennenlotter J, Wiesner T, Just L, Bonin M, et al. Generation of pluripotent stem cells from adult human testis. Nature. 2008 Nov. 20; 456(7220):344-9.

Coura G S, Garcez R C, de Aguiar C B, Alvarez-Silva M, Magini R S, Trentin A G. Human periodontal ligament: A niche of neural crest stem cells. J Periodontal Res. 2008 October; 43(5):531-6.

D'Angelo F, Armentano I, Mattioli S, Crispoltoni L, Tiribuzi R, Cerulli G G, Palmerini C A, Kenny J M, Martino S, Orlacchio A. Micropatterned hydrogenated amorphous carbon guides mesenchymal stem cells towards neuronal differentiation. Eur Cell Mater. 2010 Oct. 5; 20:231-44.

Degistirici O, Jaquiery C, Schönebeck B, Siemonsmeier J, Götz W, Martin I, Thie M. Defining properties of neural crest-derived progenitor cells from the apex of human developing tooth. Tissue Eng Part A. 2008 February; 14(2):317-30.

Dupin E, Coelho-Aguiar J M. Isolation and differentiation properties of neural crest stem cells. Cytometry A. 2012 Jul. 26.

Huang C Y, Pelaez D, Dominguez-Bendala J, Garcia-Godoy F, Cheung H S. Plasticity of stem cells derived from adult periodontal ligament. Regen Med. 2009 November; 4(6):809-21.

Jang S, Cho H H, Cho Y B, Park J S, Jeong H S. Functional neural differentiation of human adipose tissue-derived stem cells using bFGF and forskolin. BMC Cell Biol. 2010 Apr. 16; 11:25.

Jiang Y, Jahagirdar B N, Reinhardt R L, Schwartz R E, Keene C D, Ortiz-Gonzalez X R, et al. Pluripotency of mesenchymal stem cells derived from adult marrow. Nature. 2002 Jul. 4; 418(6893):41-9.

Kim S U, de Vellis J. Stem cell-based cell therapy in neurological diseases: a review. J Neurosci Res. 2009 Aug. 1; 87(10):2183-200.

Kuo Y C, Chang Y H. Differentiation of induced pluripotent stem cells toward neurons in hydrogel biomaterials. Colloids Surf B Biointerfaces. 2012 Sep. 6; 102C:405-411.

Kuo Y C, Wang C T. Neuronal differentiation of induced pluripotent stem cells in hybrid polyester scaffolds with heparinized surface. Colloids Surf B Biointerfaces. 2012 Dec. 1; 100:9-15.

Li, X.-W., Tian, Y.-H Amplification and directional differentiation in vitro of human umbilical cord blood derived mesenchymal stem cells into neuron-like cells. Journal of Clinical Rehabilitative Tissue Engineering Research, 2009; 13 (1): 57-60.

Mruthyunjaya S, Manchanda R, Godbole R, Pujari R, Shiras A, Shastry P. Laminin-1 induces neurite outgrowth in human mesenchymal stem cells in serum/differentiation factors-free conditions through activation of FAK-MEK/ERK signaling pathways. Biochem Biophys Res Commun. 2010 Jan. 1; 391(1):43-8.

Nejsum L N, Praetorius J, Nielsen S, NKCC1 and NHE1 are abundantly expressed in the basolateral plasma membrane of secretory coil cells in rat, mouse, and human sweat glands. Am J Physiol Cell Physiol. 2005 August; 289(2):C333-40.

Ostrakhovitch E A, Byers J C, O'Neil K D, Semenikhin O A. Directed differentiation of embryonic P19 cells and neural stem cells into neural lineage on conducting PEDOT-PEG and ITO glass substrates. Arch Biochem-Biophys. 2012 Aug. 25; 528(1):21-31.

Qian D X, Zhang H T, Ma X, Jiang X D, Xu R X. Comparison of the efficiencies of three neural induction protocols in human adipose stromal cells. Neurochem Res. 2010 April; 35(4):572-9.

Rezanejad H, Matin M M. Induced pluripotent stem cells: Progress and future perspectives in the stem cell world. Cell Reprogram. 2012 Oct. 4.

Ribeiro D, Laguna Goya R, Ravindran G, Vuono R, Parish C L, Foldi C, Piroth T, Yang S, Parmar M, Nikkhah G, Hjerling-Leffler J, Lindvall O, Barker R A, Arenas E. Efficient expansion and dopaminergic differentiation of human fetal ventral midbrain neural stem cells by midbrain morphogens. Neurobiol Dis. 2012 Aug. 24; 49C: 118-127.

Ruiz S, Diep D, Gore A, Panopoulos A D, Montserrat N, Plongthongkum N, et al. Identification of a specific reprogramming-associated epigenetic signature in human induced pluripotent stem cells. Proc Natl Acad Sci USA. 2012 Oct. 2; 109(40):16196-201.

Seo B M, Miura M, Gronthos S, Bartold P M, Batouli S, Brahim J, Young M, Robey P G, Wang C Y, Shi S. Investigation of multipotent postnatal stem cells from human periodontal ligament. Lancet. 2004 Jul. 10-16; 364(9429):149-55.

Song J S, Kim S O, Kim S H, Choi H J, Son H K, Jung H S, Kim C S, Lee J H. In vitro and in vivo characteristics of stem cells derived from the periodontal ligament of human deciduous and permanent teeth. Tissue Eng Part A. 2012 October; 18(19-20):2040-51.

Takahashi K, Tanabe K, Ohnuki M, Narita M, Ichisaka T, Tomoda K, et al. Induction of pluripotent stem cells from adult human fibroblasts by defined factors. Cell. 2007 11/30; 131 (0092-8674; 5):861-72.

Taneyhill L A. To adhere or not to adhere: the role of Cadherins in neural crest development. Cell Adh Migr. 2008 October-December; 2(4):223-30.

Tucker B A, I H Park, S D Qi, H J Klassen, C Jiang, J Yao, S Redenti, G Q Daley and M J Young. Transplantation of adult mouse iPS cell-derived photoreceptor precursors restores retinal structure and function in degenerative mice. PLoS One 2011 6:e18992.

Wagers A J, Weissman I L. Plasticity of adult stem cells. Cell. 2004 Mar. 5; 116(5):639-48.

Wen X, Liu L, Deng M, Zhang L, Liu R, Xing Y, et al. Characterization of p75(+) ectomesenchymal stem cells from rat embryonic facial process tissue. Biochem Biophys Res Commun. 2012 Sep. 12.

Xu X, Li W E, Huang G Y, Meyer R, Chen T, Luo Y, et al. Modulation of mouse neural crest cell motility by N-cadherin and connexin 43 gap junctions. J. Cell Biol. 2001 Jul. 9; 154(1):217-30.

Zhou Y, Chen K S, Gao J B, Han R, Lu J J, Peng T, Jia Y J. [miR-124-1 promotes neural differentiation of rat bone marrow mesenchymal stem cells]. Zhongguo Dang Dai ErKeZaZhi. 2012 March; 14(3):215-20. Chinese.

---

The invention claimed is:

1. A method of isolating pluripotent stem cells comprising:
   extracting cells from tissue derived from the neural crest, wherein the tissue derived from the neural crest is adult periodontal ligament or dental pulp from exfoliated deciduous teeth;
   culturing said extracted cells under adherent conditions; and
   isolating said cultured cells that express Connexin-43, wherein said isolating is
   performed using a reagent with an affinity for said Connexin-43 to obtain a population of said cultured cells that express Connexin-43, wherein said population comprises at least 80% pluripotent stem cells.

2. The method of claim 1, further comprising screening said extracted cells for expression of Connexin-43, at least one stem cell marker, or at least one neural crest marker prior to isolation.

3. The method of claim 2, wherein said at least one stem cell marker or neural crest marker is Oct4, Nanog, Sox2, Klf4, p75 neurotrophin receptor, Nestin, Sox10, N-Cadherin, Notch1, BMP2, Snail, Slug, or combinations thereof.

4. The method of claim 1, wherein said isolated stem cells are capable of differentiating into cells of the ectoderm, endoderm, and mesoderm lineages and generating teratomas when injected into immunodeficient mice.

5. A method of repairing damaged tissue in a subject in need thereof comprising administering to said subject pluripotent stem cells isolated using the method of claim 1.

6. The method of claim 5, wherein the stem cells are autologous.

7. The method of claim 5, wherein said damaged tissue is neural tissue, retinal tissue, skeletal muscle tissue, cardiac tissue, bone or cartilage.

* * * * *

SEQUENCE LISTING

```
<160> NUMBER OF SEQ ID NOS: 46

<210> SEQ ID NO 1
<211> LENGTH: 22
<212> TYPE: DNA
<213> ORGANISM: Artificial Sequence
<220> FEATURE:
<223> OTHER INFORMATION: Synthetic construct

<400> SEQUENCE: 1
gatgcctctg gtggggtatt tc                                              22

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
tttccttctg tcgctggtgc                                                 20

<210> SEQ ID NO 3
<211> LENGTH: 18
<212> TYPE: DNA
<213> ORGANISM: Artificial Sequence
<220> FEATURE:
<223> OTHER INFORMATION: Synthetic construct

<400> SEQUENCE: 3
tgctggattc tcacacac                                                   18

<210> SEQ ID NO 4
```

```
<211> LENGTH: 22
<212> TYPE: DNA
<213> ORGANISM: Artificial Sequence
<220> FEATURE:
<223> OTHER INFORMATION: Synthetic construct

<400> SEQUENCE: 4
ctcgtcagga ataatgaaca ag                                              22

<210> SEQ ID NO 5
<211> LENGTH: 18
<212> TYPE: DNA
<213> ORGANISM: Artificial Sequence
<220> FEATURE:
<223> OTHER INFORMATION: Synthetic construct

<400> SEQUENCE: 5
atcagatgac attaagac                                                   18

<210> SEQ ID NO 6
<211> LENGTH: 18
<212> TYPE: DNA
<213> ORGANISM: Artificial Sequence
<220> FEATURE:
<223> OTHER INFORMATION: Synthetic construct

<400> SEQUENCE: 6
cttcagtgat tctaggat                                                   18

<210> SEQ ID NO 7
<211> LENGTH: 23
<212> TYPE: DNA
<213> ORGANISM: Artificial Sequence
<220> FEATURE:
<223> OTHER INFORMATION: Synthetic construct

<400> SEQUENCE: 7
aactgtgtag gaatgtatat gtg                                             23

<210> SEQ ID NO 8
<211> LENGTH: 22
<212> TYPE: DNA
<213> ORGANISM: Artificial Sequence
<220> FEATURE:
<223> OTHER INFORMATION: Synthetic construct

<400> SEQUENCE: 8
attagcaaca accagaataa gt                                              22

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
caagttctgg gaagtcatca                                                 20

<210> SEQ ID NO 10
<211> LENGTH: 19
<212> TYPE: DNA
<213> ORGANISM: Artificial Sequence
<220> FEATURE:
<223> OTHER INFORMATION: Synthetic construct

<400> SEQUENCE: 10
```
ttgtagtaga cgctgatcc                                                    19

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
ttggcaaggg aaacaaacac                                                   20

<210> SEQ ID NO 12
<211> LENGTH: 24
<212> TYPE: DNA
<213> ORGANISM: Artificial Sequence
<220> FEATURE:
<223> OTHER INFORMATION: Synthetic construct

<400> SEQUENCE: 12
tcagggaaat tgggatgtat atgt                                              24

<210> SEQ ID NO 13
<211> LENGTH: 22
<212> TYPE: DNA
<213> ORGANISM: Artificial Sequence
<220> FEATURE:
<223> OTHER INFORMATION: Synthetic construct

<400> SEQUENCE: 13
attcaacgaa gcccactacc ca                                                22

<210> SEQ ID NO 14
<211> LENGTH: 22
<212> TYPE: DNA
<213> ORGANISM: Artificial Sequence
<220> FEATURE:
<223> OTHER INFORMATION: Synthetic construct

<400> SEQUENCE: 14
atccttggct gacttgagga tc                                                22

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
ctaccctctc aacgacagca                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
gttcctcctc agagtcgctg                                                   20

<210> SEQ ID NO 17
<211> LENGTH: 20
<212> TYPE: DNA

```
<213> ORGANISM: Artificial Sequence
<220> FEATURE:
<223> OTHER INFORMATION: Synthetic construct

<400> SEQUENCE: 17
gacagcccac tcttttgagc                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
tgggtttccc ttcatgactc                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
gaacatcatc cctgcatcca                                               20

<210> SEQ ID NO 20
<211> LENGTH: 19
<212> TYPE: DNA
<213> ORGANISM: Artificial Sequence
<220> FEATURE:
<223> OTHER INFORMATION: Synthetic construct

<400> SEQUENCE: 20
ccagtgagct tcccgttca                                                19

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
caggtgcccc agctgcttcg                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic construct

<400> SEQUENCE: 22
cccgccagcg gttattcggg                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic construct

<400> SEQUENCE: 23
caagatctcg gaccgctact                                               20
```

<210> SEQ ID NO 24
<211> LENGTH: 20
<212> TYPE: DNA
<213> ORGANISM: Artificial Sequence
<220> FEATURE:
<223> OTHER INFORMATION: Synthetic construct

<400> SEQUENCE: 24
ccgtggtcag catcttgtta                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
ctgcagagaa gagtgtcgca                                                    20

<210> SEQ ID NO 26
<211> LENGTH: 22
<212> TYPE: DNA
<213> ORGANISM: Artificial Sequence
<220> FEATURE:
<223> OTHER INFORMATION: Synthetic construct

<400> SEQUENCE: 26
ggtcttcacc tgtttgtagc tg                                                 22

<210> SEQ ID NO 27
<211> LENGTH: 22
<212> TYPE: DNA
<213> ORGANISM: Artificial Sequence
<220> FEATURE:
<223> OTHER INFORMATION: Synthetic construct

<400> SEQUENCE: 27
caggagaaac agggcctaca ga                                                 22

<210> SEQ ID NO 28
<211> LENGTH: 19
<212> TYPE: DNA
<213> ORGANISM: Artificial Sequence
<220> FEATURE:
<223> OTHER INFORMATION: Synthetic construct

<400> SEQUENCE: 28
tccagcttgg ggtcctgaa                                                     19

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
cctgagggct tcaaagtgtc                                                    20

<210> SEQ ID NO 30
<211> LENGTH: 20
<212> TYPE: DNA
<213> ORGANISM: Artificial Sequence
<220> FEATURE:

<223> OTHER INFORMATION: Synthetic construct

<400> SEQUENCE: 30
cggaacttct tggtctccag                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic construct

<400> SEQUENCE: 31
ggctccacac cttacagctc                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic construct

<400> SEQUENCE: 32
ctgggctccc tgggtagtag                                               20

<210> SEQ ID NO 33
<211> LENGTH: 22
<212> TYPE: DNA
<213> ORGANISM: Artificial Sequence
<220> FEATURE:
<223> OTHER INFORMATION: Synthetic construct

<400> SEQUENCE: 33
cttcaggaga tatgcaaagc ag                                            22

<210> SEQ ID NO 34
<211> LENGTH: 19
<212> TYPE: DNA
<213> ORGANISM: Artificial Sequence
<220> FEATURE:
<223> OTHER INFORMATION: Synthetic construct

<400> SEQUENCE: 34
gctgatctgc tgcagtgtg                                                19

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
gcagaggtcc tatcccatga                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic construct

<400> SEQUENCE: 36
ctgggtggaa agagaagctg                                               20

```
<210> SEQ ID NO 37
<211> LENGTH: 19
<212> TYPE: DNA
<213> ORGANISM: Artificial Sequence
<220> FEATURE:
<223> OTHER INFORMATION: Synthetic construct

<400> SEQUENCE: 37
cggaggtcaa caacgagtc                                                     19

<210> SEQ ID NO 38
<211> LENGTH: 20
<212> TYPE: DNA
<213> ORGANISM: Artificial Sequence
<220> FEATURE:
<223> OTHER INFORMATION: Synthetic construct

<400> SEQUENCE: 38
tctctgcctt ctgtgtggtg                                                    20

<210> SEQ ID NO 39
<211> LENGTH: 23
<212> TYPE: DNA
<213> ORGANISM: Artificial Sequence
<220> FEATURE:
<223> OTHER INFORMATION: Synthetic construct

<400> SEQUENCE: 39
gaccccaatc ggaagcctaa cta                                                23

<210> SEQ ID NO 40
<211> LENGTH: 23
<212> TYPE: DNA
<213> ORGANISM: Artificial Sequence
<220> FEATURE:
<223> OTHER INFORMATION: Synthetic construct

<400> SEQUENCE: 40
agcctttccc actgtcctca tct                                                23

<210> SEQ ID NO 41
<211> LENGTH: 20
<212> TYPE: DNA
<213> ORGANISM: Artificial Sequence
<220> FEATURE:
<223> OTHER INFORMATION: Synthetic construct

<400> SEQUENCE: 41
ttcggaccca cacattacct                                                    20

<210> SEQ ID NO 42
<211> LENGTH: 20
<212> TYPE: DNA
<213> ORGANISM: Artificial Sequence
<220> FEATURE:
<223> OTHER INFORMATION: Synthetic construct

<400> SEQUENCE: 42
gcagtgaggg caagaaaaag                                                    20

<210> SEQ ID NO 43
<211> LENGTH: 20
<212> TYPE: DNA
<213> ORGANISM: Artificial Sequence
<220> FEATURE:
<223> OTHER INFORMATION: Synthetic construct
```

```
<400> SEQUENCE: 43
cccccctgtg gttacctctt                                                    20

<210> SEQ ID NO 44
<211> LENGTH: 21
<212> TYPE: DNA
<213> ORGANISM: Artificial Sequence
<220> FEATURE:
<223> OTHER INFORMATION: Synthetic construct

<400> SEQUENCE: 44
gctgggacat gtgaagtctg c                                                  21

<210> SEQ ID NO 45
<211> LENGTH: 20
<212> TYPE: DNA
<213> ORGANISM: Artificial Sequence
<220> FEATURE:
<223> OTHER INFORMATION: Synthetic construct

<400> SEQUENCE: 45
acctcaacca cctggtatcg                                                    20

<210> SEQ ID NO 46
<211> LENGTH: 20
<212> TYPE: DNA
<213> ORGANISM: Artificial Sequence
<220> FEATURE:
<223> OTHER INFORMATION: Synthetic construct

<400> SEQUENCE: 46
ttcttggcat cgaacatctg                                                    20
```